US008343493B2

(12) United States Patent
VanMechelen et al.

(10) Patent No.: US 8,343,493 B2
(45) Date of Patent: Jan. 1, 2013

(54) ANTIBODIES SPECIFIC OF THE β-AMYLOID PEPTIDES AND THEIR USES AS DIAGNOSTIC AGENTS OR DRUGS

(75) Inventors: Eugeen VanMechelen, Nazareth-Eke (BE); Pierre Grognet, Bruxelles Evere (BE); Nicolas Sergeant, Ronchin (FR); Marie Gompel, Lille (FR); Andre Delacourte, Faches Thumesnil (FR); Luc Buee, Templemars (FR); Laurent Pradier, Verrieres (FR); Veronique Blanchard-Bregeon, Paris (FR)

(73) Assignees: Innogenetics N.V., Gent-Zwijnaarde (BE); INSERM (Institut National de la Sante et de la Recherche Medicale), Paris (FR); Sanofi, Paris (FR)

( * ) Notice: Subject to any disclaimer, the term of this patent is extended or adjusted under 35 U.S.C. 154(b) by 0 days.

(21) Appl. No.: 12/740,217

(22) PCT Filed: Oct. 24, 2008

(86) PCT No.: PCT/EP2008/064432
§ 371 (c)(1),
(2), (4) Date: Nov. 24, 2010

(87) PCT Pub. No.: WO2009/056490
PCT Pub. Date: May 7, 2009

(65) Prior Publication Data
US 2011/0059092 A1    Mar. 10, 2011

(30) Foreign Application Priority Data
Oct. 29, 2007    (EP) ..................................... 07119537

(51) Int. Cl.
A61K 39/395    (2006.01)
C12P 21/08    (2006.01)
C07K 16/18    (2006.01)
C12N 5/20    (2006.01)
C12N 5/12    (2006.01)
G01N 33/533    (2006.01)
G01N 33/534    (2006.01)
G01N 33/535    (2006.01)

(52) U.S. Cl. .............. 424/141.1; 424/139.1; 530/388.25; 530/388.1; 530/387.9; 530/391.3; 530/391.1; 435/331; 435/337

(58) Field of Classification Search ........................ None
See application file for complete search history.

(56) References Cited

U.S. PATENT DOCUMENTS
2007/0098721 A1*  5/2007 Hillen et al. ............... 424/145.1

FOREIGN PATENT DOCUMENTS
WO    2004/013172    2/2004

OTHER PUBLICATIONS

Akiyama H et al. (1999) Occurrence of the diffuse amyloid beta-protein (Abeta) deposits with numerous Abeta-containing glial cells in the cerebral cortex of patients with Alzheimer's disease. Glia, 25:324-331.*
Alberts B, et al. Molecular Biology of the Cell, Third Edition, 1994, pp. 1216-1220.*
Kuby J. Immunology, Third Edition, 1997, W.H. Freeman & Co., New York, pp. 131-134.*
Padlan EA et al. Strucure of an antibody-antigen complex: crystal structure of the HyHEL-10 Fab-lysozyme complex. Proc Natl Acad Sci USA, 1989; 86:5938-5942.*
Paul, WE, Editor. Fundamental Immunology, Third Edition, 1993, Raven Press, New York, pp. 292-295.*
Rudikoff S et al. Single amino acid substitution altering antigen-binding specificity. Proc Natl Acad Sci USA, 1982; 79(6):1979-1983.*
"Antibodies to Beta Amyloid Proteins" Internet Citation, [Online] Jun. 3, 2002, XP002557888, Retrieved from the Internet: URL:web.archive.org/web/20020626154443/www.alzforum.org/members/resources/antibodies/Beta-Amyloid/table.html> [retrieved on Oct. 15, 2003].
Kiyoko S. Murayama et al., "A novel monoclonal antibody specific for the amino-truncated beta-amyloid Abeta5-40/42 produced from caspase-cleaved amyloid precursor protein", Journal of Neuroscience Methods, Elsevier Science Published B.V., Amsterdam, NL, vol. 161, No. 2, Mar. 27, 2007, pp. 244-249, XP022002199, ISSN: 0165-270.
Nicolas Sergeant et al., "Truncated beta-amyloid peptide species in pre-clinical Alzheimer's disease as new targets for the vaccination approach", Journal of Neurochemistry, New York, NY, US, vol. 85, No. 6, Jun. 2003, pp. 1581-1591, XP002257887, ISSN: 0022-3042.
International Search Report dated Mar. 5, 2009, from corresponding PCT application.

* cited by examiner

Primary Examiner — Elizabeth C Kemmerer
Assistant Examiner — Kimberly A Ballard
(74) Attorney, Agent, or Firm — Young & Thompson

(57) ABSTRACT

A monoclonal antibody which specifically binds to the N-terminal region of $A\beta_{8-x}$ peptide, x being included from 11 to 42, and recognizes neither $A\beta_{1-40}$ nor $A\beta_{1-42}$ and which presents a high affinity with respect to $A\beta_{8-x}$ peptide, such as determined by an immunological complex formation between the monoclonal antibody and the peptide $A\beta_{8-x}$.

17 Claims, 13 Drawing Sheets

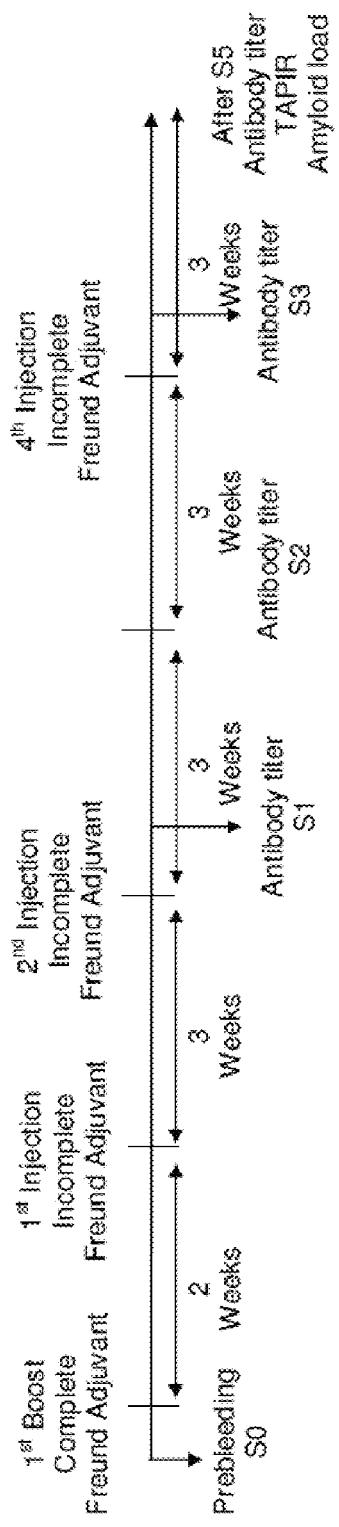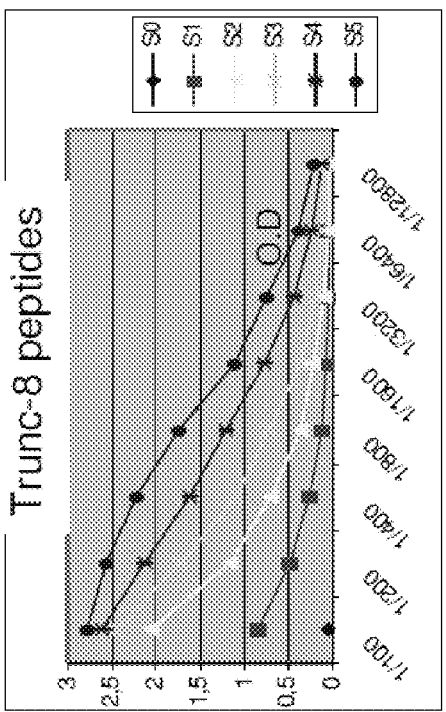
Figure 2

ANTIBODIES SPECIFIC OF THE β-AMYLOID PEPTIDES AND THEIR USES AS DIAGNOSTIC AGENTS OR DRUGS

The present invention relates to new antibodies specific of the β-amyloid peptides and their uses as diagnostic agents or drugs.

Amyloidosis refers to a pathological condition in a mammal characterized by the presence of amyloid fibers. Amyloid is a generic term referring to a group of diverse but specific protein deposits. All amyloid deposits have common morphologic properties, stain with specific dyes (e.g. Congo red), and have a characteristic red-green birefringent appearance in polarized light after staining. Different amyloids are also characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of prion protein (referred to as AScr or PrP-27) in the central nervous system. Similarly, Alzheimer's disease, another neurodegenerative disorder, is characterized by neuritic plaques and neurofibrillary tangles. In this case, the plaque and blood vessel amyloid is formed by the deposition of fibrillar β-amyloid protein.

Alzheimer's disease (AD) is the most common type of senile dementia and is believed to be responsible for 40-60% of all cases of dementia. The incidence of AD increases with age, affecting 1 out of 10 persons older than age 65 and nearly 1 out of 2 persons older than age 85. Overall, the natural history of the disease can be characterized as an irreversibly progressive brain disorder that ultimately results in devastating memory loss, profound behavioural and personality changes, and severely damaged cognitive abilities. These impairments are related to the underlying death of brain cells and the breakdown of communication between them. In view of the large expenses for health care systems that must provide institutional and ancillary care for the AD patients, the impact of AD on society and on national economies is enormous.

Two major types of histological lesions are observed in AD brains, in association with neuronal loss (Felician and Sandson, (1999). The neurobiology and pharmacotherapy of Alzheimer's disease. J. Neuropsychiatry Clin. Neurosci. 11: 19-31):

(i) at the intracellular level, the neuronal cytoskeleton in AD patients is progressively disrupted and replaced by neurofibrillary tangles (NFTs) composed of paired helical filaments (PHF);

(ii) at the extracellular level, amyloid plaques are formed by deposits of fibrillary β-amyloid (Aβ).

Aβ is a major component of the senile plaques. Aβ is a small peptide found mainly in two sizes, consisting of 40 ($A\beta_{1-40}$) and 42 ($A\beta_{1-42}$) amino acids respectively, and in minor amounts in other sizes. Aβ is known to be metabolised from the proteolytic cleavage of APP (Saido, (2000), Degradation of amyloid-β peptide: a key to Alzheimer pathogenesis, prevention and therapy. Neurosci. News 3: 52-62), a large transmembrane protein with known, although not completely clear, neurotrophic functions (Seo et al., (2001), Effects of nicotine on APP secretion and Abeta-or CT(105)-induced toxicity. Biol. Psychiatry 49: 240-247). APP can be cleaved via two main routes, a major non-amyloidogenic route and a minor second, amyloidogenic route that yields Aβ as ultimate product.

The main pathway for catabolism of APP is through cleavage by α-secretase at a single site in APP near the center of the β-amyloid peptide region (Esch et al., (1990), Cleavage of amyloid beta peptide during constitutive processing of its precursor. Science 248: 1122-1124; Sisodia, (1992), Beta-amyloid precursor protein cleavage by a membrane-bound protease. Proc. Natl. Acad. Sci. USA 89: 6075-6079). The products yielded by this route are a large N-terminal region of APP (APPsα) and a membrane associated C-terminal fragment (C83), which is subsequently hydrolysed by γ-secretase to yield the nearly unknown small p3 peptide. This is the non-amyloidogenic route because the cleavage site is located approximately in the middle of the Aβ sequence, with no possibility of Aβ formation. The second APP processing pathway is the N-and C-terminal cleavage of APP by β-and γ-secretase (FIG. 1). The resulting molecules of these two proteolytic steps are the central fragments of APP, $A\beta_{40}$ and $A\beta_{42}$, $A\beta_{40}$ being the more abundant of the whole Aβ formed (Conde, (2002), β-amyloid peptide as a target for treatment of Alzheimer's disease. Expert Opin. Ther. Patents 12: 503-512). β-secretase cleaves at the amino terminus of the β-amyloid peptide and occurs first, followed by γ-secretase, which releases the carboxy terminus of the peptide. This statement is based upon the observation that C-terminal fragments produced by β-secretase cleavage are readily apparent in cells, whereas APP fragments corresponding to a single C-terminal γ cleavage are not (Haass et al., (1992), Amyloid beta-peptide is produced by cultured cells during normal metabolism. Nature 359: 322-325; Seubert et al., (1992), Isolation and quantification of soluble Alzheimer's beta-peptide from biological fluids. Nature 359: 325-327).

The amyloid peptides involved in parenchymal plaque deposition are distinct from plaque deposition observed in transgenic mouse models (Sergeant, N. et al., (2003) Truncated beta-amyloid peptide species in pre-clinical Alzheimer's disease as new targets for the vaccination approach. Journal of Neurochemistry 85: 1581-1591; Kalback, W. et al., (2002) APP transgenic mice Tg2576 accumulate Abeta peptides that are distinct from the chemically modified and insoluble peptides deposited in Alzheimer's disease senile plaques. Biochemistry 41: 922-928; Rufenacht, P. et al. (2005) Quantification of the Aβ peptide in Alzheimer's plaques by laser dissection microscopy combined with mass spectrometry. J Mass Spectrom 40: 193-201).

In particular N-truncated forms of $A\beta_{42}$ are much more abundant than the full-size secretase-generated Aβ. Furthermore in model systems and in circulating fluids such as CSF and plasma an increasing number of additional Aβ peptides have been detected (Lewczuk, P. et al. (2004), Amyloid beta peptides in cerebrospinal fluid as profiled with surface enhanced laser desorption/ionization time-of-flight mass spectrometry: evidence of novel biomarkers in Alzheimer's disease. *Biol. Psychiatry. March* 1. 55, 524-530; Lewczuk, P. et al. (2004), Electrophoretic separation of amyloid beta peptides in plasma. *Electrophoresis*. 25, 3336-3343; Lewczuk, P. et al. (2003), The amyloid-beta (Abeta) peptide pattern in cerebrospinal fluid in Alzheimer's disease: evidence of a novel carboxyterminally elongated Aβ peptide. *Rapid Commun. Mass Spectrom.;* 17, 1291-1296; Wiltfang, J. et al. (2002), Highly conserved and disease-specific patterns of carboxyterminally truncated Aβ peptides 1-37/38/39 in addition to 1-40/42 in Alzheimer's disease and in patients with chronic neuroinflammation. *J. Neurochem.* 81, 481-496; Qi-Takahara, Y. et al. (2005), Longer forms of amyloid beta protein: implications for the mechanism of intramembrane cleavage by gamma-secretase. J Neurosci 25, 436-445; Funamoto, S. et al. (2004), Truncated carboxyl-terminal fragments of beta-amyloid precursor protein are processed to amyloid beta-proteins 40 and 42. Biochemistry 43, 13532-13540, Sato, T. et al. (2003), Potential link between amyloid beta-protein 42 and C-terminal fragment gamma 49-99 of beta-amyloid precursor protein. *J. Biol. Chem.* 278, 24294-24301.

Immunotherapy for Alzheimer with antibodies directed to the β-amyloid peptide is a potential new way to treat Alzheimer's disease (Schenk et al., (2000), beta-peptide immunization: a possible new treatment for Alzheimer disease. Arch Neurol 57: 934-936; Hock et al., (2003), Antibodies against beta-amyloid slow cognitive decline in Alzheimer's disease. Neuron 38: 547-554).

However since β-amyloid is a normal constituent of normal tissue and biological fluids severe side effects have halted the first clinical trials (Orgogozo et al., (2003), Subacute meningoencephalitis in a subset of patients with AD after Abeta 42 immunization. Neurology 61: 46-54).

It has been shown by Sergeant et al.(Sergeant et al., (2003), Truncated beta-amyloid peptide species in pre-clinical Alzheimer's disease as new targets for the vaccination approach. Journal of Neurochemistry 85: 1581-1591) that 60% of all Aβ species of early amyloïd deposits are amino-truncated Aβ species.

The international application WO 2004/029630 discloses a monoclonal antibody which specifically recognises $A\beta_{11-x}$ peptides and does not recognise $A\beta_{1-x}$ peptide (x being 40 or 42).

The peptides used for immunization are the first 5 to 7 human amino-acids of the β secretase_11 cleavage site (the 13 secretase cleaves the APP protein at Glu 11). Nevertheless, the $A\beta_{11-x}$ peptides are not the Aβ peptides observed at the very early stages of amyloid deposition (Sergeant et al., Truncated beta-amyloid peptide species in pre-clinical Alzheimer's disease as new targets for the vaccination approach. *Journal of Neurochemistry* 85, 1581-1591 (2003). Moreover, $A\beta_{11-x}$ is not a pathological species as it is produced from cleavage of β secretase and N-truncated forms of $A\beta_{42}$ are much more abundant than the full-size $A\beta_{42}$ and $A\beta_{11-x}$ species.

International application WO 2004/013172 relates to polyclonal antibodies directed toward truncated beta-amyloid peptide species $A\beta_{m-n}$, m being comprised from 1 to 10 and n being comprised from m+3 to m+15. The peptides used for immunization are $A\beta_{5-12}$, $A\beta_{6-13}$, $A\beta_{8-15}$, $A\beta_{9-16}$. Nevertheless antibodies of this application are polyclonal, having a moderate affinity.

Murayama K. S. et al. (Murayama K. S. et al., (2007), A novel monoclonal antibody specific for the amino-truncated β-amyloid $A\beta_{5-40/42}$ produced from caspase-cleaved amyloid precursor protein, 161: 244-249) disclose a monoclonal antibody obtained with peptide $A\beta_{5-12}$ immunization, and that recognises specifically $A\beta_{5-40}$ and not $A\beta_{1-40}$.

Two other antibodies are described in this paper:
mouse monoclonal antibody 4G8 specific for $A\beta_{17-24}$;
rabbit polyclonal antibody Ab-1 specific for $A\beta_{15-30}$.
Nevertheless these two antibodies are not specific and recognize $A\beta_{5-40}$ and $A\beta_{1-40}$.

One of the aims of the present invention is to provide an antibody which specifically binds to N-terminal region of $A\beta_{8-x}$ peptide and does not recognise $A\beta_{1-x}$ (x being 40 or 42) and is able to specifically recognise the early stages peptides of β-amyloid deposit.

A further aim of the present invention is to provide synthetic peptides useful to produce an immune response against N-truncated peptides of Aβ and consequently useful for the prevention or the treatment of Alzheimer's disease.

The present invention also relates to a process of preparation in order to obtain an antibody which specifically binds to N-terminal region of $A\beta_{8-x}$ peptide.

The present invention further relates to a method for determining amyloid burden in mammals.

A further aim of the present invention is to provide a method for determining, in a mammal, the susceptibility to a disease associated with Aβ formation and/or aggregation such as Alzheimer's disease, for determining, in a mammal, the risk of developing a disease associated with β-amyloid formation and/or aggregation such as Alzheimer's disease, for screening of the clearance of β-amyloid deposition in mammal, or for predicting the level of β-amyloid burden in a mammal.

The present invention also relates to therapeutic or vaccine compositions comprising an antibody specific to N-terminal region of $A\beta_{8-x}$ peptide or comprising synthetic peptides with a free N-terminal-end mimicking the free N-terminal-end of N-truncated Aβ peptides, useful for the preparation of a drug or a vaccine intended for the prevention or the treatment of Alzheimer disease.

The present invention further relates the use of an antibody for the preparation of a drug or a vaccine intended for the prevention or the treatment of Alzheimer disease.

Therefore, the present invention relates to an antibody which specifically binds to the N-terminal region of $A\beta_{8-x}$ peptide, x being comprised from 11 to 42, and recognises neither $A\beta_{1-40}$ nor $A\beta_{1-42}$.

The term "antibody" is used to denote polyclonals or monoclonals specific to $A\beta_{8-x}$ and also include fragments or molecules which mimic the monoclonals specific to $A\beta_{8-x}$, and in particular epitope binding fragment. Fragments or molecules may be derived from monoclonals by recombinant DNA techniques or by enzymatic or chemical methods and may exhibit similar binding characteristics compared to the monoclonal for an antigen fragment.

By "polyclonal antibody" is meant an antibody derived from different B-cell lines.

By "monoclonal antibody" is meant an antibody coming from only one type of cell, the hybridoma cell.

By "hybridoma" cell is meant a cell fusion which will continually produce antibodies, i.e. tumor cells that can replicate endlessly which are fused with mammalian cells.

The antibodies of the present invention include both the full length antibodies discussed above, as well as epitope-binding fragments thereof. As used herein, "antibody fragments" include any portion of an antibody that retains the ability to bind to the epitope recognized by the full length antibody, generally termed "epitope-binding fragments." Examples of antibody fragments include, but are not limited to, Fab, Fab' and F(ab')$_2$, Fd, single-chain Fvs (scFv), single-chain antibodies, disulfide-linked Fvs (dsFv) and fragments comprising either a VL or VH region. Epitope-binding fragments, including single-chain antibodies, may comprise the variable region(s) alone or in combination with the entirety or a portion of the following: hinge region, CH1, CH2, and CH3 domains.

Such fragments may contain one or both Fab fragments or the F(ab')$_2$ fragment. Further, the fragments may be or may combine members of any one of the following immunoglobulin classes: IgG, IgM, IgA, IgD, or IgE, and the subclasses thereof.

Fab and F(ab')$_2$ fragments may be produced by proteolytic cleavage, using enzymes such as papain (Fab fragments) or pepsin (F(ab')$_2$ fragments).

The "single-chain FVs" ("scFvs") fragments are epitope-binding fragments that contain at least one fragment of an antibody heavy chain variable region ($V_H$) linked to at least one fragment of an antibody light chain variable region ($V_L$).

The linker may be a short, flexible peptide selected to assure that the proper three-dimensional folding of the $V_L$ and $V_H$ regions occurs once they are linked so as to maintain the target molecule binding-specificity of the whole antibody from which the single-chain antibody fragment is derived. The carboxyl terminus of the $V_L$ or $V_H$ sequence may be covalently linked by a linker to the amino acid terminus of a complementary $V_L$ or $V_H$ sequence.

Single-chain antibody fragments of the present invention contain amino acid sequences having at least one of the variable or complementarity determining regions (CDRs) of the whole antibodies described in this specification, but lack some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Single-chain antibody fragments may be generated by molecular cloning, antibody phage display library or similar techniques well known to the skilled artisan. These proteins may be produced, for example, in eukaryotic cells or prokaryotic cells, including bacteria. The epitope-binding fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labelled antigen bound or captured to a solid surface or bead. Phages used in these methods are typically filamentous phage including fd and M13 binding domains expressed from phage with Fab, Fv or disulfide-stabilized Fv antibody domains recombinantly fused to either the phage gene III or gene VIII protein.

Examples of phage display methods that can be used to make the epitope-binding fragments of the present invention include those disclosed in Brinkman et al., 1995, *J. Immunol. Methods,* 182: 41-50; Ames et al., 1995, *J. Immunol. Methods,* 184: 177-186; Kettleborough et al., 1994, *Eur. J. Immunol.,* 24: 952-958; Persic et al., 1997, *Gene,* 187: 9-18; Burton et al., 1994, *Advances in Immunology,* 57: 191-280; WO/1992/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology, e.g., as described in detail below. For example, techniques to recombinantly produce Fab, Fab' and F(ab')$_2$ fragments can also be employed using methods known in the art such as those disclosed in WO 92/22324; Mullinax et al., 1992, *BioTechniques,* 12(6): 864-869; Sawai et al., 1995, *AJRI,* 34: 26-34; and Better et al., 1988, *Science,* 240:1041-1043; said references incorporated by reference in their entireties. Examples of techniques which can be used to produce single-chain Fvs and antibodies include those described in U.S. Pat. Nos. 4,946,778 and 5,258,498; Huston et al., 1991, *Methods in Enzymology,* 203: 46-88; Shu et al., 1993, *PNAS,* 90: 7995-7999; Skerra et al., 1988, *Science,* 240:1038-1040.

Also included within the scope of the invention are functional equivalents of the antibodies specifically disclosed in the present application. The term "functional equivalents" includes antibodies with homologous sequences, chimeric antibodies, artificial antibodies and modified antibodies, for example, wherein each functional equivalent is defined by its ability to specifically bind to the N-terminal region of $A\beta_{8-x}$ peptide as defined above. The skilled artisan will understand that there is an overlap in the group of molecules termed "antibody fragments" and the group termed "functional equivalents." Methods of producing functional equivalents are known to the person skilled in the art and are disclosed, for example, in WO 93/21319, EP 239,400; WO 89/09622; EP 338,745; and EP 332,424, which are incorporated in their respective entireties by reference.

Artificial antibodies include scFv fragments, diabodies, triabodies, tetrabodies and mru (see reviews by Winter, G. and Milstein, C., 1991, *Nature,* 349: 293-299; Hudson, P. J., 1999, *Current Opinion in Immunology,* 11: 548-557), each of which has antigen-binding ability. In the single chain Fv fragment (scFv), the $V_H$ and VL domains of an antibody are linked by a flexible peptide. Typically, this linker peptide is about 15 amino acid residues long. If the linker is much smaller, for example 5 amino acids, diabodies are formed, which are bivalent scFv dimers. If the linker is reduced to less than three amino acid residues, trimeric and tetrameric structures are formed that are called triabodies and tetrabodies. The smallest binding unit of an antibody is a CDR, typically the CDR2 of the heavy chain which has sufficient specific recognition and binding that it can be used separately. Such a fragment is called a molecular recognition unit or mru. Several such mrus can be linked together with short linker peptides, therefore forming an artificial binding protein with higher avidity than a single mru.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. The covalent attachment does not prevent the antibody from generating an anti-idiotypic response. These modifications may be carried out by known techniques, including, but not limited to, specific chemical cleavage, acetylation, formylation, metabolic synthesis of tunicamycin, etc. Additionally, the modified antibodies may contain one or more non-classical amino acids.

Functional equivalents may be produced by interchanging different CDRs on different chains within different frameworks. Thus, for example, different classes of antibody are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework.

Functional equivalents may be readily produced by mutation, deletion and/or insertion within the variable and/or constant region sequences that flank a particular set of CDRs, using a wide variety of methods known in the art.

The antibody specific for said N-terminal region of $A\beta_{8-x}$ peptide can be detected by an immunoassay. As used herein, an "immunoassay" is an assay that utilizes an antibody to specifically bind to the antigen (i.e. the N-terminal region of $A\beta_{8-x}$ peptide). The immunoassay is thus characterized by detection of specific binding of proteins to antibodies.

The expressions "specifically binds to", "specific recognition", "specifically recognizing", "specifically reacting with" or "specifically forming an immunological reaction with" refer to a binding reaction by the antibody to the N-terminal region of $A\beta_{8-x}$ peptide, which is determinative of the presence of the N-terminal region of $A\beta_{8-x}$ peptide in the sample tested, in the presence of a heterogeneous population of other proteins and/or other biologics. The specificity can be determined by a Luminex assay. Using this assay, antibodies of the invention present a high specificity on $A\beta_{8-x}$ peptide, i.e the Mean Fluorescence Intensity (MFI) obtained with an antibody is much more higher on a $A\beta_{8-x}$ peptide than on a non-specific peptide like $A\beta_{6-13}$ peptide, for example MFI=1822 with TeiA1.1 on $A\beta_{8-15}$ peptide and only 24 on $A\beta_{6-13}$ peptide (see example 3 and table 3).

Immunological methods include but are not limited to fluid or gel precipitation reactions, immunodiffusion (single or double), agglutination assays, immunoelectrophoresis, radioimmunoassays (RIA), enzyme-linked immunosorbent assays (ELISA), Western blots, liposome immunoassays (Monroe et al., 1986), complement-fixation assays, immunoradiometric assays, fluorescent immunoassays, protein A immunoassays, or immunoPCR. An overview of different immunoassays is given in Wild D. (2001) (Wild D. (2001), The Immunoassay Handbook $2^{nd}$ edition. Nature Pr., London, UK) and Ghindilis et al. (2002) (Ghindilis A. L., Pavlov A. R., Atanassov P. B. (eds.) (2002) Immunoassay Methods and Protocols. Humana Press, Totowa, N.J., US).

Thus, under the designated immunoassay conditions, the specified antibody preferentially binds to a N-terminal region of $A\beta_{8-x}$ peptide of the invention while binding to other proteins or protein isoforms does not occur in significant amounts.

In particular, the specified antibody does not bind to $A\beta_{1-42}$ peptide and therefore would not present the severe side effects observed with antibodies against $A\beta_{1-42}$ peptide when used for therapeutic purposes (see example 5).

Such a response can be an active response induced by administration of immunogen or a passive response induced by administration of antibody or primed T-cells. A cellular immune response is elicited by the presentation of polypeptide epitopes in association with Class I or Class II MHC molecules to activated antigen-specific CD4 T helper cells and/or CD8+ cytotoxic T-cells. The response may also involve activation of monocytes, macrophages, NK cells, basophils, dendritic cells, astrocytes, microglia cells, eosinophils or components of innate immunity.

An "immunogenic agent" or "immunogen" is capable of inducing an immunological response directed against itself upon administration to a recipient mammal, optionally in conjunction with an adjuvant.

In a preferred embodiment, said antibody presents a high specificity for the free N-terminal end of $A\beta_{8-x}$ peptide.

The expression "free N-terminal end" refers to an unblocked N-terminal end i.e. an amino-acid having a $NH_2$ terminal end.

Antibodies of the invention can be polyclonal having a high specificity or monoclonal having a high specificity.

In another preferred embodiment, said antibody presents a high affinity with respect to $A\beta_{8-x}$ peptide.

The term "affinity" refers to the strength of the binding of the antibody to the N-terminal region of $A\beta_{8-x}$ peptide, i.e., how tightly the antibody binds to the N-terminal region of $A\beta_{8-x}$ peptide.

Antibodies of the invention can be polyclonal having a high affinity or monoclonal having a high affinity.

The affinity of the monoclonal antibody of the invention to the N-terminal region of $A\beta_{8-x}$ peptide is determined by the bridging assay test (see example 3). OD values below 1 represent low affinity and above 1 show high affinity of the monoclonals to its target.

In another advantageous embodiment, antibodies of the invention can be polyclonal with a high specificity and a high affinity, or monoclonal with a high specificity and a high affinity.

In a more preferred embodiment, said antibody specifically target parenchymal amyloid deposits of $A\beta_{8-x}$ peptide in the brain and does not interact with vascular amyloid deposits.

The induction of an immune response is "active" when an immunogen is administered to induce antibodies or T-cells reactive against the immunogen. The induction of an immune response is "passive" when an antibody is administered that itself binds to the N-terminal truncated $A\beta_8$ peptide in the mammal.

One of the side-effects of the passive immunization is the frequency of microhemorrhages. Such increase in the number of microhemorrhages may be explained by the fixation of injected antibodies to the aggregated AB peptides within vessel walls (see example 5).

Therefore, antibodies of the invention specifically targeting parenchymal amyloid deposits and not vascular amyloid deposits would not present the severe side effects observed with antibodies against $A\beta_{1-42}$ peptide (see example 5).

In a preferred embodiment, the present invention relates to an antibody wherein x is comprised from 15 to 42, in particular a monoclonal antibody.

In a preferred embodiment, the present invention relates to a monoclonal antibody which specifically binds to the N-terminal region of $A\beta_{8-x}$ peptide, wherein the variable region comprises one of the following pairs of amino acid sequences, corresponding respectively to the light and heavy chain:

Areas in grey corresponds to the Complementarity Determining Regions of the light chain (CDR-Lx) or the heavy chain (CDR-Hx)

Antibody TeiA 1.6 (Secreted by Hybridoma IGH521)
Light Chain Variable Region:

(SEQ ID NO: 1)

CDR-L1      CDR-L2
SSLTVTAGEKVTMSCKSSQSLLAGRYQKNYLTWYQQKPGQPPKLLIYWAST

CDR-L3
RDSGVPDRFTGSGSGTDFTLTISSVQAEDLAVYYCQNDYTYPLTFAG

Heavy Chain Variable Region:

(SEQ ID NO: 2)
```
              CDR-H1                      CDR-H2
GGLVQPGGSLRLSCAISGFTFSDFYMEWVRQPPGKRLEWIAASRNKANDYT
                                    CDR-H3
TEYSASVKGRFIVSRDTSQSILYLQMNALRAEDTAIYYCATYHDYAMDYW
GQGTSVTVSS
```

Antibody TeiA 1.7 (Secreted by Hybridoma IGH522)
Light Chain Variable Region:

(SEQ ID NO: 3)
```
                      CDR-L1
SSLTVTAGEKVTMNCKSSQNLLNSGNQVNYLTWFQQKPGQPPKLLIYWAST
   CDR-L2                       CDR-L3
RESGVPDRFIGSGSGTDFTLTINSVQAEDLAVYYCQNDYRYPLTFGAG
```

Heavy Chain Variable Region:

(SEQ ID NO: 4)
```
              CDR-H1                      CDR-H2
GGLVQPGGSLRLSCATSGFTFSDFYMEWVRQPPGRRLEWIAASRDKAKDY
                                    CDR-H3
TTEYSASVKGRFIVSRDTSQSIFYLQMNALRSEDTAIYYCATYFSYAMDY
WGLTSVTVSS
```

Antibody TeiA 1.8 (Secreted by Hybridoma IGH523)
Light Chain Variable Region:

(SEQ ID NO: 5)
```
                 CDR-L1                   CDR-L2
SSLAVTAGERVTMSCKSSLTLLNSGSQTNYLTWYQQKPGQPPKLLIYWAS
                 CDR-L3
TRESGVPDRFTGSGSGTDFTLTISSVQAEDLAVYYCQNDYSYPLTFGAG
```

Heavy Chain Variable Region:

(SEQ ID NO: 6)
```
              CDR-H1                      CDR-H2
GGLVQPGGSLRLSCATAGFTFTDQYMSWVRQPPGKALEWLATIRNKAKGFT
                                    CDR-H3
TEYSASVKGRFTISRDNSQSILYLQMSTLRAGDSATYYCAVYGNYAMDYWG
QGTSVNVSS
```

Antibody TeiA 2b.6 (Secreted by Hybridoma IGH524)
Light Chain Variable Region:

(SEQ ID NO: 7)
```
                   CDR-L1                    CDR-L2
SSLTVTAGEKVTMSCKSSQSLFNSGRQTNYLTWFQQRPGQAPKLLIYWAS
                 CDR-L3
TRGSGVPDRFTGSGSGTEFTLTISSVQAEDLAVYYCQNDYTYPLTFGAG
```

Heavy Chain Variable Region:

(SEQ ID NO: 8)
```
              CDR-H1                      CDR-H2
GGLVQPGGSLRLSCATSGFTFTDFYMEWVRQPPGKRLEWIAASRNKANGY
                                    CDR-H3
TTEYSASVKGRFIVSRDTSQGILYLQMSALRAEDTAIYYCAIYRYYAMDY
WGQGTSVTVSS
```

Antibody TeiA 1.1 (Secreted by Hybridoma IGH525)
Light Chain Variable Region:

(SEQ ID NO: 9)
```
                         CDR-L1                CDR-L2
SSLTVTAGEKVTMSCTSSQSLFNSGTQTNYLTWYQQKPGQPPKLLIYWAS
                 CDR-L3
TRESGVPDRFTGSGSGTDFTLTISSVQAEDLAVYYCQNDYTYPLTFGAG
```

Heavy Chain Variable Region:

(SEQ ID NO: 10)
```
              CDR-H1                      CDR-H2
GGLVQPGGSLRLSCATSGFTFSDFFIEWVRQPPGKRLEWITASRNKMYDY
                                    CDR-H3
KTEYSASVKGRFIVSRDTSQSILYLQMNALRAEDTAIYYCAIYRMYAMDY
WGQGTSVTVSS
```

As used herein, an "antibody" refers to a protein consisting of one or more polypeptides substantially encoded by immunoglobulin genes or fragments of immunoglobulin genes.

In a preferred embodiment, the CDR of the light and heavy chain of the variable region of the antibody defined above comprises one of the following amino acid sequences:

Antibody TeiA 1.6 (IGH521 Sequence)
CDR of the Light Chain Variable Region:

```
CDR-L1:
KSSQSLLAGRYQKNYLT   (SEQ ID NO: 11)
CDR-L2:
WASTRDSG            (SEQ ID NO: 12)
CDR-L3:
QNDYTYPLT           (SEQ ID NO: 13)
```

CDR of the Heavy Chain Variable Region:

```
CDR-H1:
GFTFSDFYME          (SEQ ID NO: 14)
CDR-H2:
ASRNKANDYTTEYSASVKG (SEQ ID NO: 15)
CDR-H3:
YHDYAMDY            (SEQ ID NO: 16)
```

Antibody TeiA 1.7 (IGH522 Sequence)
CDR of the Light Chain Variable Region:

```
CDR-L1:
KSSQNLLNSGNQVNYLT   (SEQ ID NO: 17)
CDR-L2:
WASTRESG            (SEQ ID NO: 18)
CDR-L3:
QNDYRYPLT           (SEQ ID NO: 19)
```

CDR of the Heavy Chain Variable Region:

```
CDR-H1:
GFTFSDFYME          (SEQ ID NO: 14)
CDR-H2:
ASRDKAKDYTTEYSASVKG (SEQ ID NO: 20)
CDR-H3:
YFSYAMDY            (SEQ ID NO: 21)
```

Antibody TeiA 1.8 (IGH523 Sequence)
CDR of the Light Chain Variable Region:

```
CDR-L1:
KSSLTLLNSGSQTNYLT   (SEQ ID NO: 22)
CDR-L2:
WASTRESG            (SEQ ID NO: 18)
CDR-L3:
QNDYSYPLT           (SEQ ID NO: 23)
```

CDR of the Heavy Chain Variable Region:

```
CDR-H1:
GFTFTDQYMS          (SEQ ID NO: 24)
CDR-H2:
TIRNKAKGFTTEYSASVKG (SEQ ID NO: 25)
CDR-H3:
YGNYAMDY            (SEQ ID NO: 26)
```

Antibody TeiA 2b.6 (IGH524 Sequence)
CDR of the Light Chain Variable Region:

```
CDR-L1:
KSSQSLFNSGRQTNYLT   (SEQ ID NO: 27)
CDR-L2:
WASTRGS             (SEQ ID NO: 28)
CDR-L3:
QNDYTYPLT           (SEQ ID NO: 13)
```

CDR of the Heavy Chain Variable Region:

```
CDR-H1:
GFTFTDFYME          (SEQ ID NO: 29)
CDR-H2:
ASRNKANGYTTEYSASVKG (SEQ ID NO: 30)
CDR-H3:
YRYYAMDY            (SEQ ID NO: 31)
```

Antibody TeiA 1.1 (IGH525 Sequence)
CDR of the Light Chain Variable Region:

```
CDR-L1:
TSSQSLFNSGTQTNYLT   (SEQ ID NO: 32)
CDR-L2:
WASTRESG            (SEQ ID NO: 18)
CDR-L3:
QNDYTYPLT           (SEQ ID NO: 13)
```

CDR of the Heavy Chain Variable Region:

```
CDR-H1:
GFTFSDFFIE          (SEQ ID NO: 33)
CDR-H2:
ASRNKNYDYKTEYSASVKG (SEQ ID NO: 34)
CDR-H3:
YRHYAMDY            (SEQ ID NO: 35)
```

The CDRs of the present invention include not only those completely identical but also variants so long as the specificity to Aβ$_{8-x}$ peptide is maintained. That is, the CDR amino acid sequences in which one or more amino acid residues are modified may also be used as the CDR sequence. The modified amino acid residues in the amino acid sequences of the CDR variant are preferably 30% or less, more preferably 20% or less, most preferably 10% or less, within the entire CDR.

Therefore, any antibody, fragment, molecule or ligand comprising at least one of the indicated CDR's or homologous sequences can be used.

The CDRs are of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made.

Several studies have surveyed the effects of introducing one or more amino acid changes at various positions in the sequence of an antibody, based on the knowledge of the primary antibody sequence, on its properties such as binding and level of expression (Yang, W. P. et al., 1995, *J. Mol. Biol.*, 254: 392-403; Rader, C. et al., 1998, *Proc. Natl. Acad. Sci. USA*, 95: 8910-8915; Vaughan, T. J. et al., 1998, *Nature Biotechnology*, 16: 535-539).

In these studies (so called affinity maturation techniques), equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology*, 16: 535-539; Adey, N. B. et al., 1996, Chapter 16, pp. 277-291, in "Phage Display of Peptides and Proteins", Eds. Kay, B. K. et al., Academic Press). These methods of changing the sequence of the primary antibody have resulted in improved affinities of the secondary antibodies (Gram, H. et al., 1992, *Proc. Natl. Acad. Sci. USA,* 89: 3576-3580; Boder, E. T. et al., 2000, *Proc. Natl. Acad. Sci. USA,* 97: 10701-10705; Davies, J. and Riechmann, L., 1996, *Immunotechnolgy,* 2: 169-179; Thompson, J. et al., 1996, *J. Mol. Biol.,* 256: 77-88; Short, M. K. et al., 2002, *J. Biol. Chem.,* 277: 16365-16370; Furukawa, K. et al., 2001, *J. Biol. Chem.,* 276: 27622-27628).

By a similar directed strategy of changing one or more amino acid residues of the antibody, the antibody sequences described in this invention can be used to develop antibodies which specifically bind to the N-terminal region of $A\beta_{8-x}$ peptide as defined above with improved functions, including improved affinity to the N-terminal region of $A\beta_{8-x}$ peptide.

Preferred amino acid substitutions are those which: (1) reduce susceptibility to proteolysis, (2) reduce susceptibility to oxidation, (3) alter binding affinity for forming protein complexes, and (4) confer or modify other physico-chemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain (s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., 1991, Nature, 354: 105, which are each incorporated herein by reference.

Improved antibodies also include those antibodies having improved characteristics that are prepared by the standard techniques of animal immunization, hybridoma formation and selection for antibodies with specific characteristics.

It is also possible to use cell lines specifically engineered for production of improved antibodies. In particular, these lines have altered regulation of the glycosylation pathway, resulting in antibodies which are poorly fucosylated or even totally defucosylated. Such cell lines and methods for engineering them are disclosed in e.g. Shinkawa et al. (2003, *J. Biol. Chem.* 278(5): 3466-3473), Ferrara et al. (2006, *J. Biol. Chem.* 281(8): 5032-5036; 2006, *Biotechnol. Bioeng.* 93(5): 851-61), EP 1331266, EP 1498490, EP 1498491, EP 1676910, EP 1792987, and WO 99/54342.

In another preferred embodiment, the present invention relates to an antibody which specifically binds to the N-terminal region of $A\beta_{8-x}$ peptide, said antibody being labelled with a compound chosen from the group comprising: a radionuclide, a fluor, an enzyme label, an enzyme substrate, an enzyme co-factor, enzyme inhibitor and a hapten.

The particular label or detectable group used in the assay is generally not a critical aspect of the invention, so long as it does not significantly interfere with the specific binding of the antibody used in the assay. The detectable group can be any material having a detectable physical or chemical property. Such detectable labels have been well developed in the field of immunoassays and, in general, almost any label useful in such methods can be applied to the method of the present invention.

Thus, a label is any composition detectable by spectroscopic, photochemical, biochemical, immunochemical, electrical, optical, radiological or chemical means. Useful labels in the present invention include but are not limited to magnetic beads (e.g. Dynabeads™), fluorescent dyes (e.g. fluorescein isothiocyanate, texas red, rhodamine), radiolables (e.g. $^3H$, $^{125}I$, $^{35}S$, $^{14}C$, or $^{32}P$), enzymes (e.g. horseradish peroxidase, alkaline phosphatase and others commonly used in an ELISA), and colorimetric labels such as colloidal gold, colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, the available instrumentation and disposal provisions. Non-radioactive labels are often attached by indirect means.

Generally, a ligand molecule (e.g. biotin) is covalently bound to the antibody. The ligand then binds to an anti-ligand (e.g. streptavidin) molecule, which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, a haptenic or antigenic compound can be used in combination with an antibody.

The antibodies can also be conjugated directly to signal-generating compounds, for example, by conjugation with an enzyme or fluorophore. Enzymes of interest as labels will primarily be hydrolases, particularly phosphatases, esterases and glycosidases, or oxidoreductases, particularly peroxidases.

Fluorescent compounds include fluorescein and its derivatives, rhodamine and its derivatives, dansyl, umbelliferone, etc. Chemiluminescent compounds include luciferin, and 2,3-dihydrophtalazinediones, for example, luminol. A review of other labeling or signal producing systems is available in U.S. Pat. No. 4,391,904.

Means for detecting labels are well known in the art. Thus, for example, where the label is a radioactive label, means for detection include a scintillation counter or photographic film as in autoradiography. Where the label is a fluorescent label, it may be detected by exciting the fluorophore with the appropriate wavelength of light and detecting the resulting fluorescence. The fluorescence may be detected visually, by means of a photographic film, by the use of electronic detectors such as charge coupled devices (CCDs) or photomultipliers and the like.

Similarly, enzyme labels may be detected by providing the appropriate substrates for the enzyme and detecting the resulting reaction product. Finally simple colorimetric labels may be detected simply by observing the color associated with the label. In a preferred embodiment, the monoclonal antibody is a humanised antibody.

By "humanised antibody" is meant a genetically engineered antibody in which the minimum mouse part from a murine antibody is transplanted onto a human antibody; generally humanized antibodies are 5-10% mouse and 90-95% human.

Humanized antibodies have the advantage to counter the HAMA (human Antibodies directed against mouse antibodies) and HACA (human antibodies directed against chimeric antibodies) responses seen with murine and chimeric antibodies and exhibit minimal or no response of the human immune system against them.

According to another aspect, the present invention concerns hybridomas producing monoclonal antibodies as above defined, i.e. which specifically binds to N-terminal region of $A\beta_{8-x}$ peptide and does not recognise neither $A\beta_{1-40}$ nor $A\beta_{1-42}$, and in particular the variable region of which comprises one of the pairs of the amino acid sequences defined above and which presents a high specificity.

In a preferred embodiment, the above defined hybridoma have been deposited on Aug. 23, 2007,
at:
BCCM/LMBP Plasmid Collection
Department of Molecular Biology
Ghent University
'Fiers-Schell-Van Montagu' building
Technologiepark 927
B-9052 Gent—Zwijnaarde
BELGIUM
under the following Accession No:
TeiA 1.6 or 2.6F4C2 (IGH521)-->LMBP 6594CB
TeiA 1.7 or 2.8A3F8 (IGH522)-->LMBP 6595CB
TeiA 1.8 or 1.3B12H3 (IGH523)-->LMBP 6596CB
TeiA 2b.6 or 2.13E5E4 (IGH524)-->LMBP 6597CB
TeiA 1.1 or 3.46B10E7 (IGH 525)-->LMBP 6598CB According to another aspect, the present invention refers to a peptide preparation to generate an immune response giving rise to an antibody production which is efficient to reduce the amyloid deposits and to isolate a monoclonal antibody.

By "peptide preparation" is meant a short synthetic peptide with a free N-terminal-end which mimics the free N-terminal-end of N-truncated Aβ peptides.

The peptide used is the following: Aβ 8-x mimicking peptide: SGYGVHHGC-KLH (SEQ ID NO: 36)

Whereas KLH is keyhole limpet hemocyanin which is coupled to the cysteine by disulfide bridge. The sequence corresponding to Aβ is underlined and followed by spacer amino-acid that is a glycine. $A\beta_{8-x}$ is similar to IGP-2119 (PG127) Table 2

The peptide preparation was mixed in phosphate saline buffer and added with Freund adjuvant for intraperitoneal injections (FIG. 2). After 24 weeks, the immune response was analyzed by TAPIR (FIG. 3) and the effect on the amyloid load was determined by western blotting (FIG. 4).

According to another aspect, the present invention relates to a process of preparation of the above defined antibody which specifically binds to the N-terminal region of $A\beta_{8-x}$ peptide and does not recognise $A\beta_{1-42}$, x being comprised from 11 to 42, in particular 15-42, which present a high specificity, and comprising an immunisation step of an appropriate animal with a $A\beta_{8-x}$ peptide and a T-helper epitope, in particular with a $A\beta_{8-x}$ peptide fused with a T-helper epitope, or a $A\beta_{8-x}$ branched peptide, in particular a $A\beta_{8-15}$ peptide.

The expression "$A\beta_{8-x}$ peptide fused with a T-helper epitope" refers to the linking of the $A\beta_{8-x}$ peptide with a T-helper epitope according to Livingston et al., (2002) containing a terminal cysteine for coupling to KLH.

The expression "$A\beta_{8-x}$ branched peptide" refers to a $A\beta_{8-x}$ peptides linked with a peptide spacer containing a terminal cysteine for coupling to KLH.

It was not obvious for the person skilled in the art to prepare the above defined antibodies because following a conventional process, i.e. immunization with five peptides ($A\beta_{1-8}$, $A\beta_{5-13}$, $A\beta_{6-14}$, $A\beta_{8-15}$, and $A\beta_{9-17}$), no specific antibody secreting hybridomas could be isolated and therefore it was necessary to immunize with a $A\beta_{8-x}$ peptide and a T-helper epitope, in particular a $A\beta_{8-x}$ peptide fused with a T-helper epitope, or to immunize with a $A\beta_{8-x}$ branched peptide.

In a preferred embodiment, the present invention relates to the process of preparation of an antibody above defined, wherein said antibody binds specifically to the N-terminal region of $A\beta_{8-15}$ peptide, does not recognise $A\beta_{1-42}$ and which presents a high affinity with respect to $A\beta_{8-15}$ peptide, such as determined on Western Blot.

A "Western blot" is a method to detect a specific protein in a given sample of tissue homogenate or extract.

According to another aspect, the present invention relates to an antibody which binds specifically to the N-terminal region of $A\beta_{8-x}$ peptide, such as obtained by a process defined above.

According to another aspect, the present invention relates to a method for determining in vitro amyloid burden in a mammal, comprising the following steps:
 (i) quantifying the level of N-terminal truncated $A\beta_{8-x}$ in a body fluid of said mammal, using the antibody as defined above,
 (ii) comparing the level of antibody of said mammal to those obtained with a control mammal, and
 (iii) deducing from step (ii) if said mammal is suffering from a neurological disease provided the N-terminal truncated $A\beta_8$, level is modified with respect to the level measured in the control mammal, in particular is higher than the level measured in the control mammal.

The mammal examined in the present invention may be a non-human mammal, such as (but not limited to) a cow, a pig, a sheep, a goat, a horse, a monkey, a rabbit, a hare, a dog, a cat, a mouse, a rat, an elk, a deer, or a tiger. In a preferred embodiment, the mammal is a primate.

In a preferred embodiment, the mammal of the above defined method is a human, more preferably the mammal is a human adult.

In another preferred embodiment, the present invention relates to the above defined method wherein specificity and sensitivity of said antibody toward $A\beta_{8-42}$ is higher than 60%, preferably comprised from about 60 to about 100%, more preferably comprised above 80%.

The term "sensitivity" refers to the degree of detection of $A\beta_{8-42}$ peptide that the method can detect. (See Neurobiology of aging, Vol 19, N°. 2, p109-116, 1998: Consensus report of the working group on: "Molecular and biochemical markers of AD"). This working group sets standards for diagnostic kit in AD and mentions that sensitivity and specificity should be >80%.

In another preferred embodiment, said body fluid of the above defined method is cerebrospinal fluid (CSF) or blood.

The term "cerebrospinal fluid" or "CSF" is intended to include whole cerebrospinal fluid or derivatives of fractions thereof well known to those skilled in the art. Thus, a cerebrospinal fluid sample can include various fractionated forms of cerebrospinal fluid or can include various diluents added to facilitate storage or processing in a particular assay. Such diluents are well known to those skilled in the art and include various buffers, preservatives and the like.

According to another aspect, the present invention relates to a method for determining, in a mammal, the susceptibility to a disease associated with β-amyloid formation and/or aggregation such as Alzheimer's disease, for determining, in a mammal, the risk of developing a disease associated with β-amyloid formation and/or aggregation such as Alzheimer's disease, for screening of the clearance of β-amyloid deposition in a mammal, or for predicting the level of β-amyloid burden in a mammal, said method comprising the following steps:
(i) determining, in said mammal, the amount of peptide $A\beta_{8-x}$ with an antibody defined above,
(ii) comparing the amount determined in step (i) with the amount of antibody specific of said N-terminal region of $A\beta_{8-x}$ peptide in a control mammal, and
(iii) concluding from the comparison in step (ii), whether the mammal is susceptible to a disease associated with β-amyloid formation and/or aggregation such as Alzheimer's disease, whether the mammal is at risk of developing a disease associated with β-amyloid formation and/or aggregation such as Alzheimer's disease, whether the β-amyloid deposition in a mammal is cleared, or what the level of β-amyloid is in said mammal.

An increase in the level of N-terminal truncated $A\beta_{8-x}$ in the brain of the tested mammal, for example, could be an indication of the mammal being susceptible to or at risk of developing a disease associated with β-amyloid formation and/or aggregation. It could also indicate that the Aβ deposition in the mammal is not yet cleared.

Increased levels of N-terminal truncated $A\beta_{8-x}$ in certain body fluids after vaccination or therapy, are an indication of the level of Aβ burden (DeMattos et al., 2002). N-terminal APP soluble fragment will mainly be found in certain body fluids. The presence of these N-terminal APP soluble fragments indicates an aberrant cleavage of APP, resulting in the formation of N-terminal truncated Aβ variants and, consequently, in an increased susceptibility to or risk of developing a disease associated with β-amyloid formation and/or aggregation by the mammal.

In a preferred embodiment, the amount of antibody specific of the N-terminal region of $A\beta_{8-x}$ peptide using the above defined method is determined on a tissue sample obtained from said mammal.

By "tissue" is meant brain tissue.

According to another aspect, the present invention relates to a kit comprising at least one buffer, and at least one detection compound, at least one N-truncated $A\beta_{8-x}$ specific antibody as defined above.

In a preferred embodiment, the kit defined above, further comprises a preferably labelled second antibody which binds to the above defined antibody.

For example, the antibodies can be bound directly to a solid substrate where they are immobilized. These immobilized antibodies then capture the N-terminal truncated $A\beta_{8-x}$ peptide of the invention present in the sample, which are subsequently detected with a second antibody.

In another aspect, the present invention relates to a therapeutic composition comprising as active ingredient an above defined antibody, or synthetic peptides with a free N-terminal-end mimicking the free N-terminal-end of N-truncated Aβ peptides, in association with a pharmaceutically acceptable vehicle.

The amount of antibody to be administered or delivered to an individual should be sufficient to cause a significant reduction in β amyloid levels in the brain of the individual. The appropriate amount will depend upon various parameters (e.g. the particular antibody used, the weight of the individual and the levels of endogenous β amyloid) and is to be determined on the case by case basis.

The dosage and frequency of administration can also vary depending on whether the treatment is prophylactic or therapeutic.

In a preferred embodiment, the above defined therapeutic composition is suitable for the administration to an individual of a dose of an antibody from 1 mg/kg/day to 200 mg.

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present antibodies can be administered prophylactically to the general population without any assessment of the risk of the subject patient. The present antibodies are especially useful for individuals who do have a known genetic risk of Alzheimer's disease. Such individuals include those having relatives who have experienced this disease and those whose risk is determined by analysis of genetic or biochemical markers.

Administration of the antibodies according to the present invention to an individual can be made via intravenous administration.

Another way of delivering to the brain is via direct infusion of the antibodies according to the present invention into the brain of the individual.

According to another aspect, the invention relates to a vaccine composition comprising as active ingredient an above defined antibody, fragments or derivatives thereof, or synthetic peptides with a free N-terminal-end mimicking the free N-terminal-end of N-truncated Aβ peptides, in association with a pharmaceutically acceptable vehicle.

In a preferred embodiment, the above defined vaccine composition is suitable for the administration to an individual of a dose of an antibody from 1 mg/kg/day to 200 mg/kg/day.

The vaccine or therapeutic compositions of the present invention induce an immune response against the specific N-terminal truncated $A\beta_{8-x}$ peptide of the invention.

According to another aspect, the present invention relates to the use of at least one of the above defined antibodies, for the preparation of a drug or a vaccine intended for the prevention or the treatment of Alzheimer disease.

As used herein, the term "preventing a disease" means inhibiting or reversing the onset of the disease, inhibiting or reversing the initial signs of the disease (i.e. formation and/or aggregation of Aβ variants), inhibiting the appearance of clinical symptoms of the disease.

As used herein, the term "treating a disease" includes substantially inhibiting the disease, substantially slowing or reversing the progression of the disease, substantially ameliorating clinical symptoms of the disease or substantially preventing the appearance of clinical symptoms of the disease.

According to another aspect, the present invention relates to the use of at least one of the above defined antibodies, for the preparation of a drug or a vaccine intended for the clearance of β amyloid burden.

The term "clearance of β amyloid burden" means that the β amyloid burden is eliminated from the brain tissue. Clearance of amyloid deposits in the brain of AD patients using vaccination against Aβ peptide is a novel approach that opens treatment perspectives (Schenk et al., 2001, Immunotherapy with beta-amyloid for Alzheimer's disease: a new frontier. DNA Cell Biol. 20: 679-681).

According to another aspect, the present invention relates to a method of clearance of β-amyloid burden in a mammal comprising the administration of an above defined composition to the said mammal.

According to another aspect, the present invention relates to the use of peptide composition defined above for induction of an immune response in a mammal being affected by or susceptible to develop an Alzheimer disease.

DESCRIPTION OF THE FIGURES

FIGS. 2A and 2B represent the schedule of intraperitoneal injections of the peptide preparation (2A) and the antibody titer measured for each bleeding (2B).
x-axis: serum dilution
y-axis: optical density

EXAMPLES

Example 1

Immunization of Double Transgenic Mice with N-Trunc 8 Peptide Preparation and Consequences on the Brain Amyloid Load Double APP Swedish London×Presenilin 1 trangenic mice (Blanchard et al., 2003 Exp Neurology 184:247; WO0120977) were injected every three weeks with 50 μg of N-Trunc 8 peptides (FIG. 2A). The whole duration of immunization was of 21 weeks. As negative and positive controls, series of mice were injected with phosphate buffer saline or aggregated Aβ$_{1-42}$ peptide, respectively. The antibody titer was determined by direct ELISA against the Trunc 8 peptides (FIG. 2B).

Figure 1:
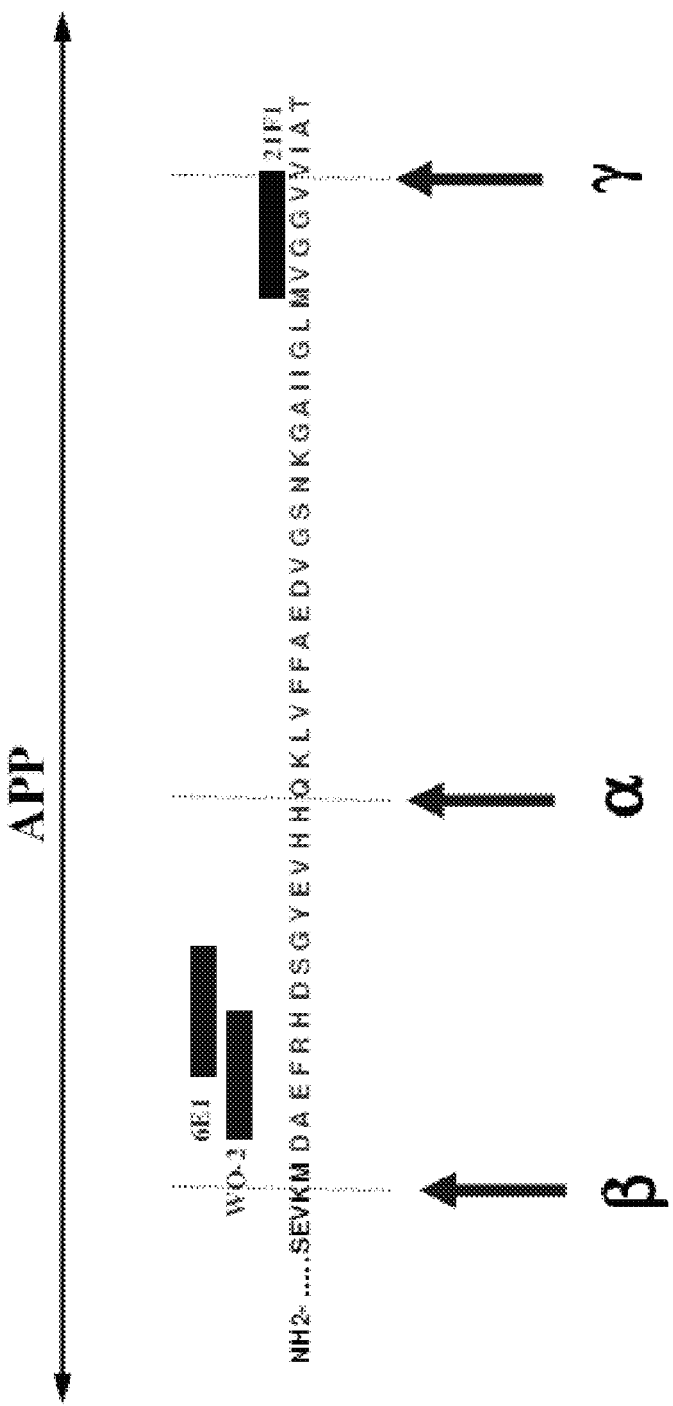
FIG. 1 represents the partial amino acid sequence of APP770, SEKVMDAEFRHDSGYEVHHQKLVFFAED-VGSNKGAIIGLMVGGVVIAT (SEQ ID NO: 37), displaying the amino acid sequence of Aβ with the α-, β-, and γ-secretase cleavage sites indicated.
Figure 3:
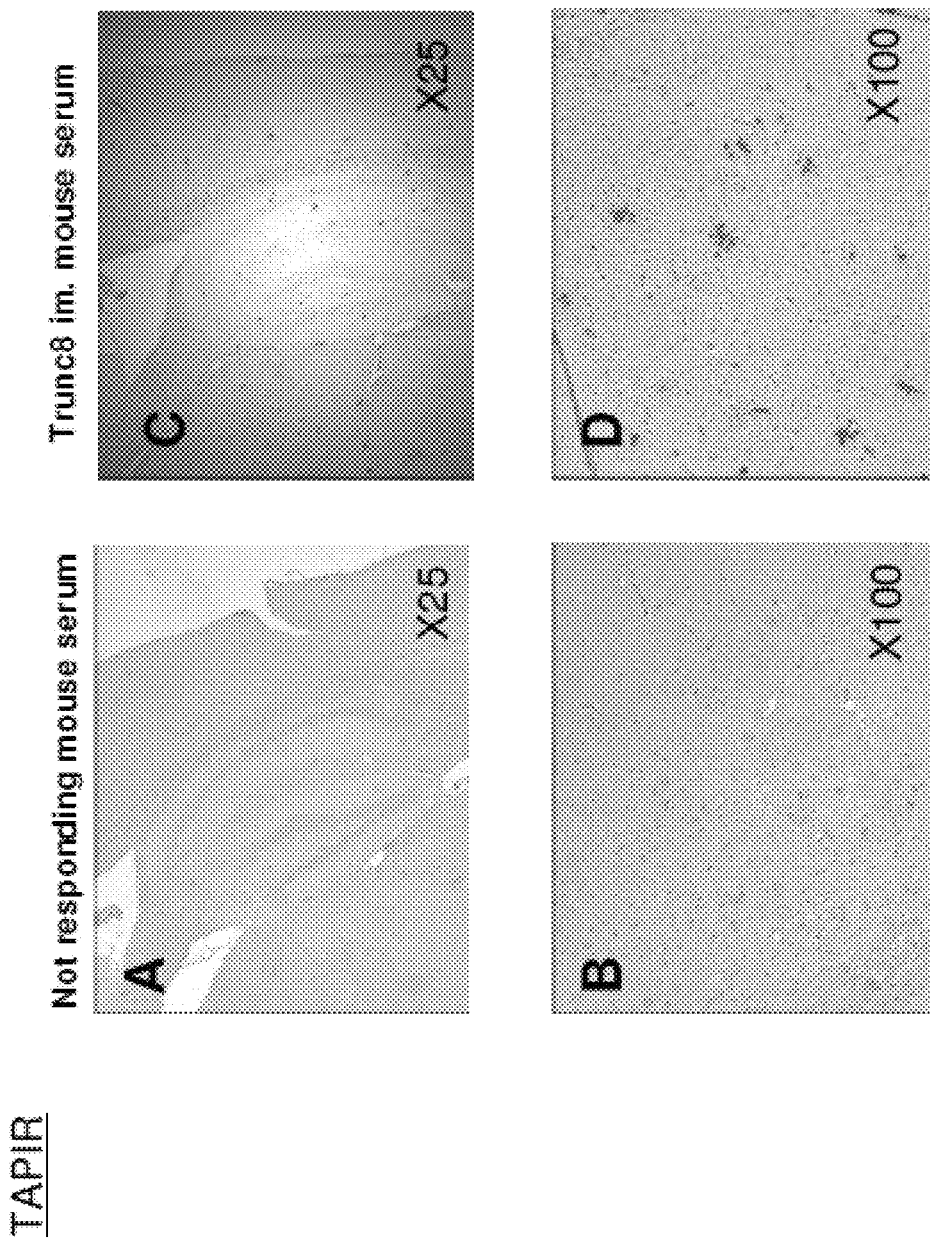
FIG. 3A to 3D represent the use of immunized mice sera to detect or not amyloid deposits in brain tissue of double transgenic APP×PS1 mice:
3A and 3B: Not responding mouse serum (magnification: ×25 and ×100 respectively),
3C and 3D: Trunc8 immunized mouse serum (magnification: ×25 and ×100 respectively).

Sera from fifth bleeding of immunized mice was used to perform tissue amyloid plaque immunoreactivity (TAPIR) (Christoph Hock, Roger M. Nitsch, Clinical Observations with AN-1792 Using TAPIR Analyses Neurodegenerative Diseases 2005; 2:273-276) (FIG. 3). The serum from a non-responding mouse was used as a negative control. Amyloid deposits were detected with the sera obtained from mice immunized with Trunc-8 peptides.

Figure 4:
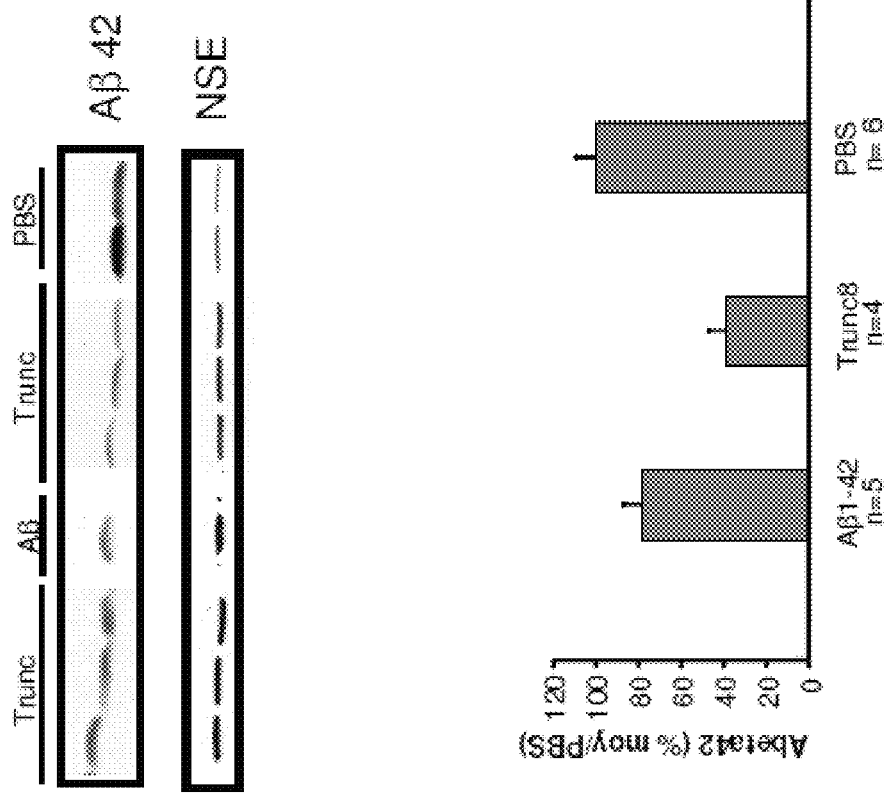
FIGS. 4A and 4B represent the Aβ load measured by western-blotting in immunized and control mice (4A) and the histogram represents the efficiency of immunization expressed the percentage of Aβ-42 load to the control condition (PBS).
Figure 5:
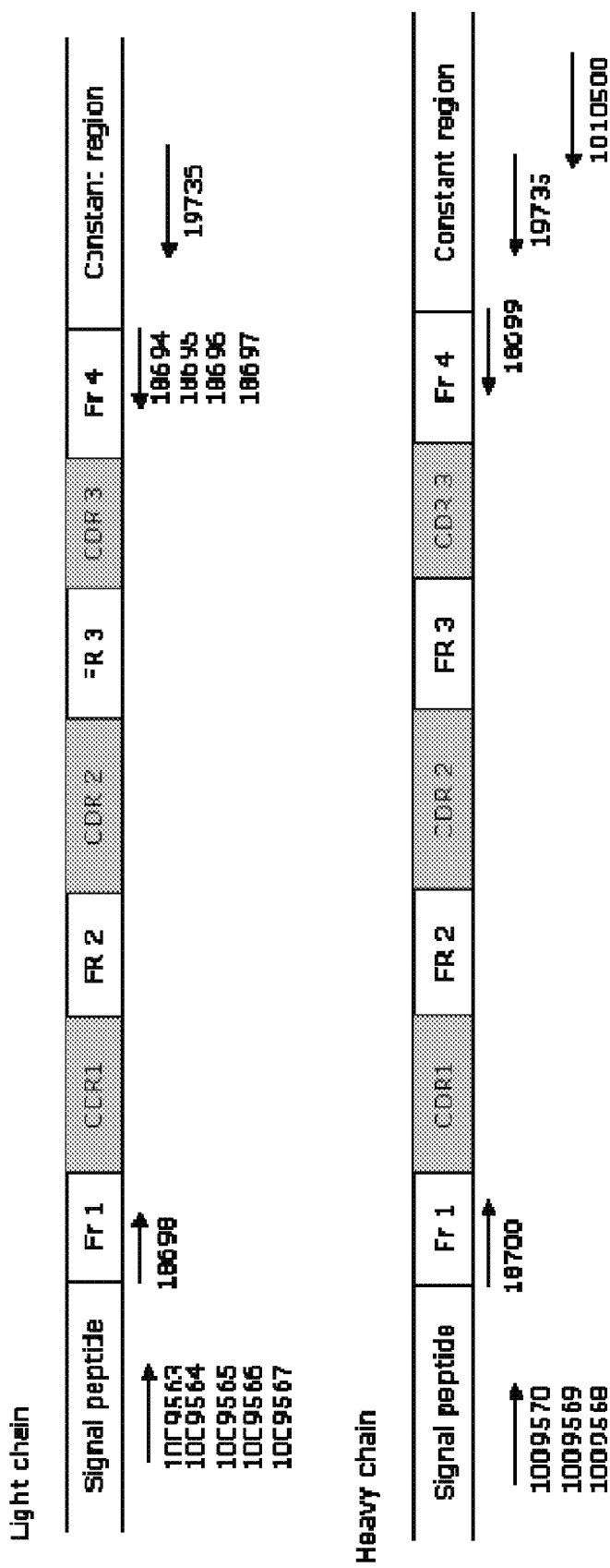
FIG. 5 the schematic overview of primer location for the light chain and the heavy chain.

Consequences of immunization on the Aβ load was examined using formic acid extracts of Aβ peptides and detection by Western-blotting as previously described (Casas et al., 2004) (FIG. 4A). The amount total Aβ-42 was measured and compared to control condition (PBS) and expressed as the percentage to the control condition (100%). The histogram represents the quantifications for each experimental condition (FIG. 4B).

Example 2

Characterization of Monoclonal Antibodies Variable Regions from Hybridoma's IGH524, IGH525, IGH521, IGH522, IGH523

The results of DNA sequence analysis was evaluated by translation of the appropriate open reading frame to amino acid sequence and alignment with consensus antibody heavy and light chain framework regions.

Data Analysis

Raw sequencing data (DNA chromatograms) are generated with Sequencing Analysis Software v5.2 (Applied Biosystems) and the KB basecaller v1.2 (Applied Biosystem) and interpreted and edited using Sequencher 4.1.2. In general, double-stranded sequencing results were assembled and the consensus sequence was linked to the Innogenetics Lotus Notes Custom Sequencing Service Request (CSSR) database and stored with the assigned CSSR project number.

Results

RNA isolation, RT-PCR, cloning and deposit.

Table 1 shows for each hybridoma/MAb the origin and source of the cells used for RNA extraction, and shows for each heavy or light antibody chain the corresponding primer combination which successfully resulted in a specific clonable PCR fragment.

Sequence Analysis

For each variable region, DNA sequence analysis and subsequent alignment revealed a possible consensus for each hybridoma/MAb. Complementary-determining regions (CDR) were identical for all clones specifying one variable region.

An overview and alignment of the obtained final consensus sequences is given in appendix 1. Theoretically predicted CDR loops are indicated (based on consensus sequence rules).

The complementarity-determining regions (CDR) as marked in the consensus sequences were assigned based on a set of public available rules from the Kabat definition (Reczko et al., 1995) or a public available analysis tool for modelling (Honegger et al. 2001). The CDRs are marked for explorative/informal use only.

IGH524, TeiA 2b.6

The results obtained for the heavy and light chain of MAb TeiA 2b.6 (2.13E5E4) isolated from hybridoma IGH524, were clear with only minor ambiguities and/or differences located mainly in framework regions. The complete variable regions have been determined and the N-terminal end (including the largest part of CDR1) of both mature antibody chains were confirmed by N-terminal amino acid sequencing of the purified antibody.

IGH521 (TeiA 1.6), IGH522 (TeiA 1.7), IGH523 (TeiA 1.8), IGH525 (TeiA 1.1)

The results for all heavy and light chains of MAb TeiA 1.6 (2.6F4C2, IGH521), TeiA 1.7 (2.8A3F8, IGH522), TeiA 1.8 (1.3B12H3, IGH523) and TeiA 1.1 (3.46B10E7, IGH525) were also clear. Eight sequences of cloned PCR products were aligned and in least three identical sequences lead to the consensus sequence. The complete variable regions have been determined by alignment with the sequence obtained from hybridoma IGH524.

TABLE 1

PCR primers

| IG request # | Name | Oligonucleotide sequence (5'->3') | Reference |
|---|---|---|---|
| 1010500 | Rev-CH-IgG1-2a | TGGACAGGGATCCAGAGTTC | Kabat et al. |
| 1009565 | MLALT3.RV | GRAGTCACAKACYCAGGTCTTY | Coloma et al. |
| 18700 | VH1BACK | AGGTSMARCTGCAGSAGTCWGG | Orlandi et al. |
| 18696 | MJK2FONX | CCGTTTTATTTCCAGCTTGGTCCC | Orlandi et al. |
| 19735 | mIG1rev (aa127-134) | AGTTTGGGCAGCAGATCC | Kabat et al. |
| 19736 | mIgKappaRev (aa120-125) | GTTAACTGCTCACTGCATGG | Kabat et al. |
| 18698 | VK2BACK | GACATTGAGCTCACCCAGTCTCCA | Orlandi et al |
| 18694 | MJK5FONX | CCGTTTCAGCTCCAGCTTGGTCCC | Orlandi et al |

Kabat et al. (Sequences of proteins of immunological interest. National Institutes of Health Publication No. 91-3242, 5th ed., 1991, United States Department of Health and Human Services, Bethesda, Md.)

Coloma et al. (Novel vectors for the expression of antibody molecules regions generated by polymerase chain reaction. J. Immunol. Methods, 1992; 152(1):89-104)

Orlandi et al. (Cloning immunoglobulin variable domains for expression by the polymerase chain reaction. Proc Natl Acad Sci USA. 1989 May; 86(10):3833-7)

| IGH | Name | Ab Chain | Primer pair | ICCG |
|---|---|---|---|---|
| 524 | TeiA 2b.6 (2.13E5E4) | Light | 1009565/18696 | 6152 |
|  |  | Heavy | 18700/1010500 | 6151 |
| 521 | TeiA 1.6 (2.6F4C2) | Light | 18698/18696 | 6233 |
|  |  | Heavy | 18700/19735 | 6232 |
| 522 | TeiA 1.7 (2.8A3F8) | Light | 18698/18696 | 6258 |
|  |  | Heavy | 18700/19735 | 6236 |
| 523 | TeiA 1.8 (1.3B12H3) | Light | 18698/18694 | 6235 |
|  |  | Heavy | 18700/1010500 | 6234 |
| 525 | TeiA 1.1 (3.46B10E7) | Light | 1009565/197368 | 6268 |
|  |  | Heavy | 18700/1010500 | 6231 |

APPENDIX 1

IGH524 Sequence
Light Chain Variable Region:

```
                                              (SEQ ID NO: 7)
                      CDR-L1
SSLTVTAGEKVTMSCKSSQSLFNSGRQTNYLTWFQQRPGQAPKLLIY
   CDR-L2
WASTRGSGVPDRFTGSGSGTEFTLTISSVQAEDLAVYYC
    CDR-L3
QNDYTYPLTFGAG
```

Heavy Chain Variable Region:

```
                                              (SEQ ID NO: 8)
                     CDR-H1
GGLVQPGGSLRLSCATSGFTFTDFYMEWVRQPPGKRLEWIA
       CDR-H2
ASRNKANGYTTEYSASVKGRFIVSRDTSQGILYLQMSALRAEDTAIYY
    CDR-H3
CAIYRYYAMDYWGQGTSVTVSS
```

IGH521 Sequence
Light Chain Variable Region:

```
                                              (SEQ ID NO: 1)
                      CDR-L1
SSLTVTAGEKVTMSCKSSQSLLAGRYQKNYLTWYQQKPGQPPKLLIY
   CDR-L2                                 CDR-L3
WASTRDSGVPDRFTGSGSGTDFTLTISSVQAEDLAVYYCQNDYTYPLT
FAG
```

Heavy Chain Variable Region:

```
                                              (SEQ ID NO: 2)
                     CDR-H1
GGLVQPGGSLRLSCAISGFTFSDFYMEWVRQPPGKRLEWIA
       CDR-H2
ASRNKANDYTTEYSASVKGRFIVSRDTSQSILYLQMNALRAEDTAIYYCA
    CDR-H3
TYHDYAMDYWGQGTSVTVSS
```

IGH525 Sequence
Light Chain Variable Region:

```
                                              (SEQ ID NO: 9)
                      CDR-L1
SSLTVTAGEKVTMSCTSSQSLFNSGTQTNYLTWYQQKPGQPPKLLIY
   CDR-L2                                 CDR-L3
WASTRESGVPDRFTGSGSGTDFTLTISSVQAEDLAVYYCQNDYTYPLT
FGAG
```

Heavy Chain Variable Region:

```
                                              (SEQ ID NO: 10)
                     CDR-H1
GGLVQPGGSLRLSCATSGFTFSDFFIEWVRQPPGKRLEWIT
       CDR-H2
ASRNKNYDYKTEYSASVKGRFIVSRDTSQSILYLQMNALRAEDTAIYYCA
    CDR-H3
IYRHYAMDYWGQGTSVTVSS
```

IGH522 Sequence
Light Chain Variable Region:

```
                                              (SEQ ID NO: 3)
                      CDR-L1
SSLTVTAGEKVTMNCKSSQNLLNSGNQVNYLTWFQQKPGQPPKLLIY
   CDR-L2                                 CDR-L3
WASTRESGVPDRFIGSGSGTDFTLTINSVQAEDLAVYYCQNDYRYPLT
FGAG
```

Heavy Chain Variable Region:

```
                                              (SEQ ID NO: 4)
                     CDR-H1
GGLVQPGGSLRLSCATSGFTFSDFYMEWVRQPPGRRLEWIA
       CDR-H2
ASRDKAKDYTTEYSASVKGRFIVSRDTSQSIFYLQMNALRSEDTAIYYCA
    CDR-H3
TYFSYAMDYWGLGTSVTVSS
```

IGH523 Sequence
Light Chain Variable Region:

(SEQ ID NO: 5)

CDR-L1
SSLAVTAGERVTMSCKSSLTLLNSGSQTNVLTWYQQKPGQPPKLLIY

CDR-L2                                    CDR-L3
WASTRESGVPDRFTGSGSGTDFTLTISSVQAEDLAVYYCQNDYSYPLT
FGAG

Heavy Chain Variable Region:

(SEQ ID NO: 6)

CDR-H1
GGLVQPGGSLRLSCATAGFTFTDQYMSWVRQPPGKALEWLA

CDR-H2
TIRNKAKGFTTEYSASVKGRFTISRDNSQSILYLQMSTLRAGDSATYYCA

CDR-H3
VYGNYAMDYWGQGTSVNVSS

Example 3

N-truncated 8-Specific Aβ Antibodies and (Limited) Characterization During Cloning Fifteen Balb-C mice were injected with a mixture of 5 short synthetic Aβ peptides (50 μg per mice KLH-coupled peptides). One mouse died for an unknown reason. The peptides correspond to the first eight N-terminal residues of respectively $A\beta_{1-8}$, $A\beta_{5-13}$, $A\beta_{6-14}$, $A\beta_{8-15}$, and $A\beta_{9-17}$ (see Table 2). The peptides also contained a C-terminal residue for coupling to KLH. After 5 injections titration of the sera was done in a 'coatings assay' of a mixture of peptides. Peptides were coated as a streptavidine-biotinylated peptide complex (peptides (IGP-2258, see Table 2) or as a BSA (bovine Serum Albumin)-peptide complex (PG-Nr see Table 2) and an anti-mouse antibody coupled to HRP (Jackson goat anti-mouse HRP, Cat No 115-035-071) was used for detection. Although titers were low (not shown) a first mouse was sacrificed and a fusion was performed. No specific antibody secreting hybridoma's has been isolated.

Therefore sets of mice were boosted with 'modified peptides'. Three mice were injected with the original peptide mixture, two mice were further injected with IGP-2119 KLH-coupled peptide (see Table 2).

Peptides corresponding to $A\beta_{8-15}$ were the more immunogenic out of the mixture of five, three additional peptides were thus synthesized. One corresponds to $A\beta_{1-8}$, fused to a T-helper epitope (PGPGP (Livingston et al., 2002); IGP-2406 (Table 2) and a C-terminal cysteine residue for coupling to KLH. The other peptide also contained another T-helper epitope (DGDGD (McMillan et al., 1983); IGP-2258 (Table 2). Finally a branched peptide containing a C-terminal cysteine for coupling was also synthesized (IGP-2407 (Table 2).

Each time two mice were immunized with the newly synthesized peptides. The $A\beta_{8-15}$ peptide was also coupled to E1 particles (WO 2004/013172) and used for boosting in the last two mice. Titers were again monitored with a 'coatings-assay' (results not shown). Titers to $A\beta_{8-15}$ were indeed improved in the mice boosted with the T-helper peptides and branched peptide and it was decided to use all three surviving mice for fusion. One of the mice boosted with the branched peptide died.

TABLE 2

Sequence of the peptides used and their Innogenetics reference number.

| Name | Innogenetics ref number | Sequence (Aβ sequence in bold with numbering) |
|---|---|---|
| $A\beta_{1-8}$ | IGP-2062 | $D_1AEFRHDS_8GC$ |
| $A\beta_{5-12}$ | IGP-2121 | $R_5HDSGYEV_{12}GC$ |
| $A\beta_{6-13}$ | IGP-2120 | $H_6DSGYEVH_{13}GC$ |
| $A\beta_{8-15}$ | IGP-2119 | $S_8GYEVHHQ_{15}GC$ |
| $A\beta_{9-16}$ | IGP-2122 | $G_9YEVHHQK_{16}GC$ |
| $A\beta_{8-15}DG$ | IGP-2405 | $S_8GYEVHHQ_{15}DGDGDC$ |
| $A\beta_{8-15}PG$ | IGP-2406 | $S_8GYEVHHQ_{15}GPGPGC$ |
| $A\beta_{8-15}$ branched | IGP-2407 | $(S_8GYEVHHQ_{15}DGDGD)_2KGC$ |
| $A\beta_{8-15}$-bio | IGP-2258 | $S_8GYEVHHQ_{15}GK$-biotin |
| $A\beta_{6-13}$-bio | IGP-2259 | $H_6DSGYEVH_{13}GK$-biotin |

Spleen of both mice were prepared and fused to SP2/0 cells. After plating, 66 plates (±3000 clones) were screened. During subcloning a limited number of clones, 24, were characterized using the biotinylated peptides IGP-2258 and IGP-2259 in a bridging assay and a Luminex assay. In the bridging assay, BSA coupled peptide IGP-128, PG127 (see Table 3) was used to capture one binding site of the antibody and a biotinylated peptide was used to detect the captured antibody in a so-called bridging assay. This assay gives an indication on the affinity of the antibody: a high-affinity antibody will give a higher signal than a lower affinity antibody. Indeed 'two classes' of antibodies have been identified.

To determine the specificity of the antibody a peptide was used which is shifted two amino-acids N-terminal as compared to the $A\beta_{8-15}$, the $A\beta_{6-13}$ peptide. The biotinylated versions of these peptides are used in order to capture it efficiently to avidin Luminex beads. After washing, the antibodies were revealed by an anti-mouse phyco-erythrine antibody. The results presented in Table 3 are raw data expressed as Mean Fluorescence Intensity (MFI). A value below 10 means below background, so for all antibodies tested with 'low affinity' (bridging assay OD<1), no reaction on the non-specific peptide (IGP-2259) was observed.

For the 'high-affinity antibody' a small signal was measurable on the non-specific peptide, but with a small difference between the antibodies. From the 'high-affinity' class of antibodies, three antibodies were chosen for subcloning, one IgG2b subtype and two IgG1, while from the 'low affinity' antibodies two IgG1 antibodies were selected, resulting in five antibodies for full characterization.

TABLE 3

Characterization of the N-truncated 8-specific Aβ, TeiA (Truncated eight amyloid), antibodies during cloning. The isotype was determined, reactivity in bridging assay (high OD is indicative for a high affinity) and specificity in a Luminex format on bio-peptides captured on avidin beads. The final subclone that has been used for further characterization is also indicated.

| Clone | Ig subtype | Bridging assay (OD450) | Luminex assay (MFI) | | Subclone | | IGH- |
|---|---|---|---|---|---|---|---|
| | | | IGP-2258 | IGP-2259 | | | |
| 2.13.E5 | IgG2b | 4 | 1686 | 51 | 2.13.E5.E4 | TeiA2b.6 | 524 |
| 3.46.B10 | IgG1 | 3.7592 | 1822 | 24 | 3.46.B10.E7 | TeiA1.1 | 525 |
| 2.6.F4 | IgG1 | | | | 2.6.F4.C2 | TeiA1.6 | 521 |
| 1.2.F4 | | 3.5836 | 1921.5 | 7 | | | |
| 2.15.A9 | | 3.7124 | 1628 | 16 | | | |
| 2.19.C6 | | 2.9978 | 1707 | 14 | | | |
| 2.25.H1 | | 4 | 1503.5 | 32 | | | |
| 2.28.H4 | IgG1 | 4 | 1817 | 23 | | | |
| 2.29.B4 | IgG1 | 3.5506 | 1717.5 | 26 | | | |
| 2.46.C10 | IgG1 | 3.0215 | 1619 | 13 | | | |
| 3.40.C3 | | 4 | 1758 | 20.5 | | | |
| 2.8.A3 | IgG1 | 0.2216 | 1715 | 5 | 2.8.A3.F8 | TeiA1.7 | 522 |
| 1.3B12 | IgG1 | | | | 1.3.B12.H3 | TeiA1.8 | 523 |
| 1.2.G12 | IgG1 | 0.2051 | 1617 | 6 | | | |
| 1.3.D12 | | 0.1928 | | | | | |
| 1.16.B8 | | 0.8537 | 1616 | 4 | | | |
| 2.1.G8 | | 0.162 | 1583 | 4 | | | |
| 2.28.F5 | | | 1632 | 4 | | | |
| 2.14.C2 | | | 1704.5 | 5 | | | |
| 2.14.D1 | | 0.1441 | 1642.5 | 5 | | | |
| 2.24.C4 | | 0.2304 | 561 | 3 | | | |
| 2.25.C4 | | 0.8982 | 1795 | 5 | | | |
| 2.28.B2 | IgG1 | 0.1478 | 2451.5 | 3 | | | |
| 1.3.G12 | IgG1 | | | | | | |

Example 4

Characterization of N-Truncated Eight Specific (TeiA) Antibodies

In order to further substantiate the specificity of these TeiA antibodies on Aβ, two approaches were taken: (1) 2D gelanalysis of a formic acid extract of a human Alzheimer brain and (2) a mixture of 'full-size' synthetic Aβpeptides (Anaspec) differing in their N-terminus used on a SELDI approach (Merchant et al., 2000).

Figure 6:
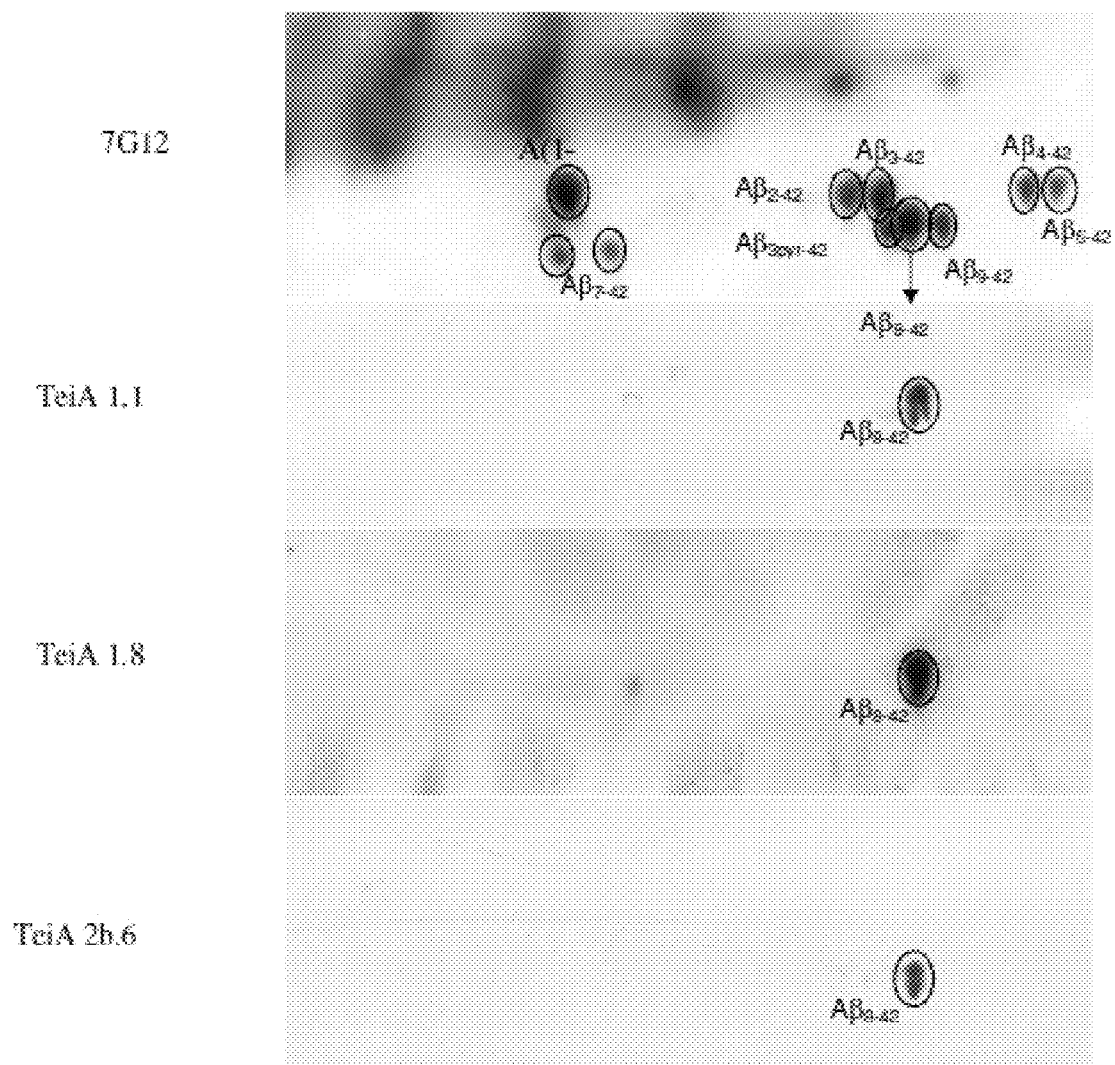
FIG. 6 represents a 2D gel analysis of a formic acid extract of a human Alzheimer brain and a mixture of "full-size" synthetic Aβ peptides ($A\beta_{2-42}$, $A\beta_{3-42}$, $A\beta_{4-42}$, $A\beta_{5-42}$, $A\beta_{7-42}$, $A\beta_{8-42}$, $A\beta_{9-42}$ (immunoblots obtained with 7G12 equivalent to 21F12 ($A\beta_{1-42}$) as described by Sergeant et al. (2003), TeiA 1.1, TeiA 1.8, and TeiA 2b.6).
Figure 7:
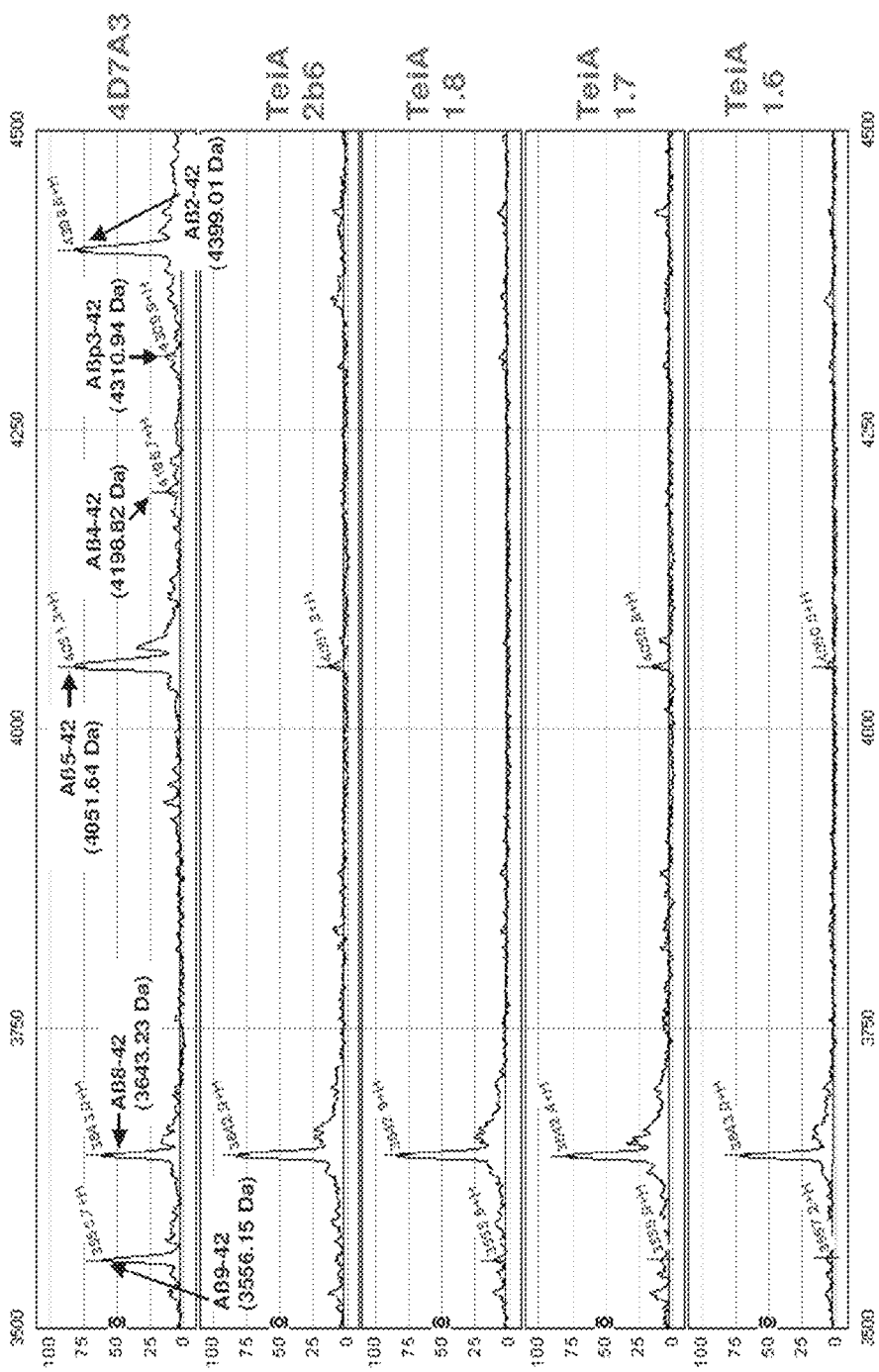
FIG. 7 represents immuno-capture antibody of 4D7A3 (a 42-C-terminal specific antibody) and TeiA 2b.6, TeiA1.8, TeiA1.7 and TeiA1.6.

The results of these approaches are shown in FIGS. 6&7. Brain tissue sampling and 2D analysis have been performed essentially as described in Sergeant et al (2003).

To reveal the position of the $A\beta_{42}$ peptides, a new 42-C-terminal specific antibody was used 7G12H1 (equivalent to 21F12 as described in Sergeant et al (2003)). The different spots have been characterized with mass-spectrometry to correspond to the different N-truncations as presented on the FIG. 6.

Figure 8:
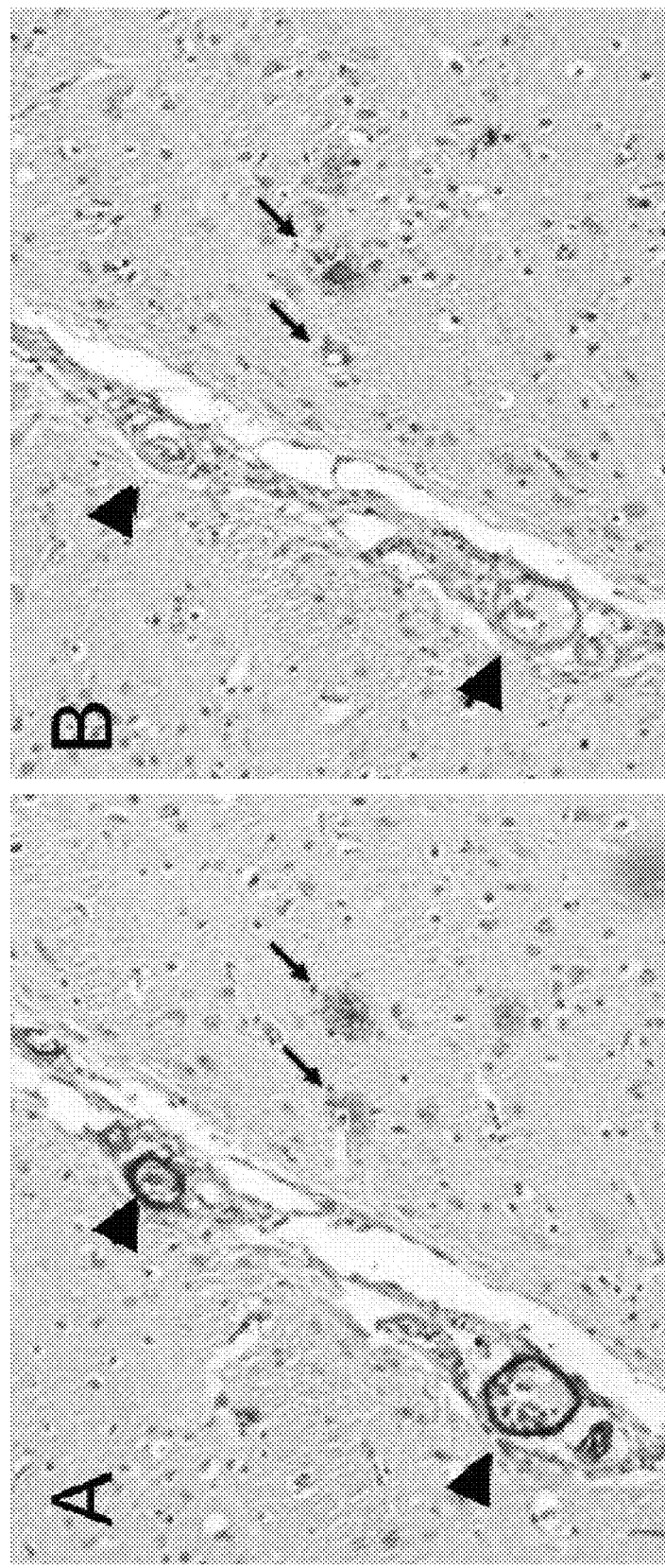
FIGS. 8A and 8B represent the specificity of the monoclonal antibody TeiA1.6 for parenchymal amyloid. 8A: labelling of both parenchymal (arrows) and vascular amyloid deposits (arrowheads) with a classical Aβ antibody 6E10.
8B: labelling of the only parenchymal (arrows) amyloïd deposits with a 8-truncated Aβ (TeiA1.6) and not the perivascular deposits (arrowheads) in an adjacent brain section.

Example 5 mAb TeiA1.6 (Aβ N-trunc8) is Specific for Parenchymal Amyloid Deposits and does not Recognize Vascular Amyloid Deposits One of the side-effects of the passive immunization is the frequency of microhemorrhages. Such increase in the number of microhemorrhages may be explained by the fixation of injected antibodies to the aggregated AB peptides within vessel walls (Paris et al., 2000; Pfeifer et al., Cerebral Hemorrhage After Passive Anti-Aβ Immunotherapy, Science 15 Nov. 2002; Vol. 298. no. 5597, p. 1379). Thus, truncated Aβ species are also original targets since they are not mainly found in amyloid angiopathy. As demonstrated in FIGS. 8A and 8B, on adjacent human AD brain sections, a classical Aβ antibody labels both parenchymal and vascular amyloid deposits (A, arrows and arrowheads, respectively, 6E10 antibody).

Using a truncated 8 antibody (B, here TeiA1.6), only parenchymal amyloid deposits are labelled (B, arrows) but not vascular amyloid deposits (B, arrowheads).

Altogether, these data indicate that amino 8-truncated AB antibodies specifically target parenchymal amyloid deposits and not interact with vascular amyloid deposits which have been suggested to be responsible for the perivascular effects (hemorraghes, encephalopathies) observed with other anti-Abeta immune approaches.

Example 6

Intracranial Administration of N-Truncated Eight Specific (TeiA) Antibodies in Transgenic Mice Lead to a Decrease in Amyloid Plaque Burden In order to demonstrate therapeutic efficacy of TeiA antibodies, they were injected in the hippocampus of transgenic mice bearing amyloid plaques in the brain and 7 day after administration, cerebral amyloid peptide plaque load was quantified by immunohistochemistry. Briefly, under stereotaxic conditions, 1 or 2 μg of antibody were injected in the right hippocampus (unilateral injection) in ThyAPP$_{SL}$× PS1$_{M146L}$ mice (Blanchard et al., 2003 Exp Neurology 184: 247; WO0120977). The antibodies injected were: two commercial classical AB antibodies (4G8 and 6E10) and the TeiA antibodies TeiA 1.1, 1.6, 1.8 and 2b6.

Seven days after injection, animals were euthanized and brains treated for immunohistochemistry. After brain postfixation, 40 µm coronal cryosections were performed and sections 400 µm apart were stained with biotinylated 4G8 anti-Abeta as a "revealing" antibody to evaluate the amyloid load present in the brain. In the case where 4G8 antibody had been injected in the brain, the revealing antibody used was biotinylated 6E10 to avoid masking of epitopes. Biotinylated antibodies were detected with a standard avidin-peroxidase detection kit (Vectastain® ABC kit Vector Laboratories).

Figure 9:
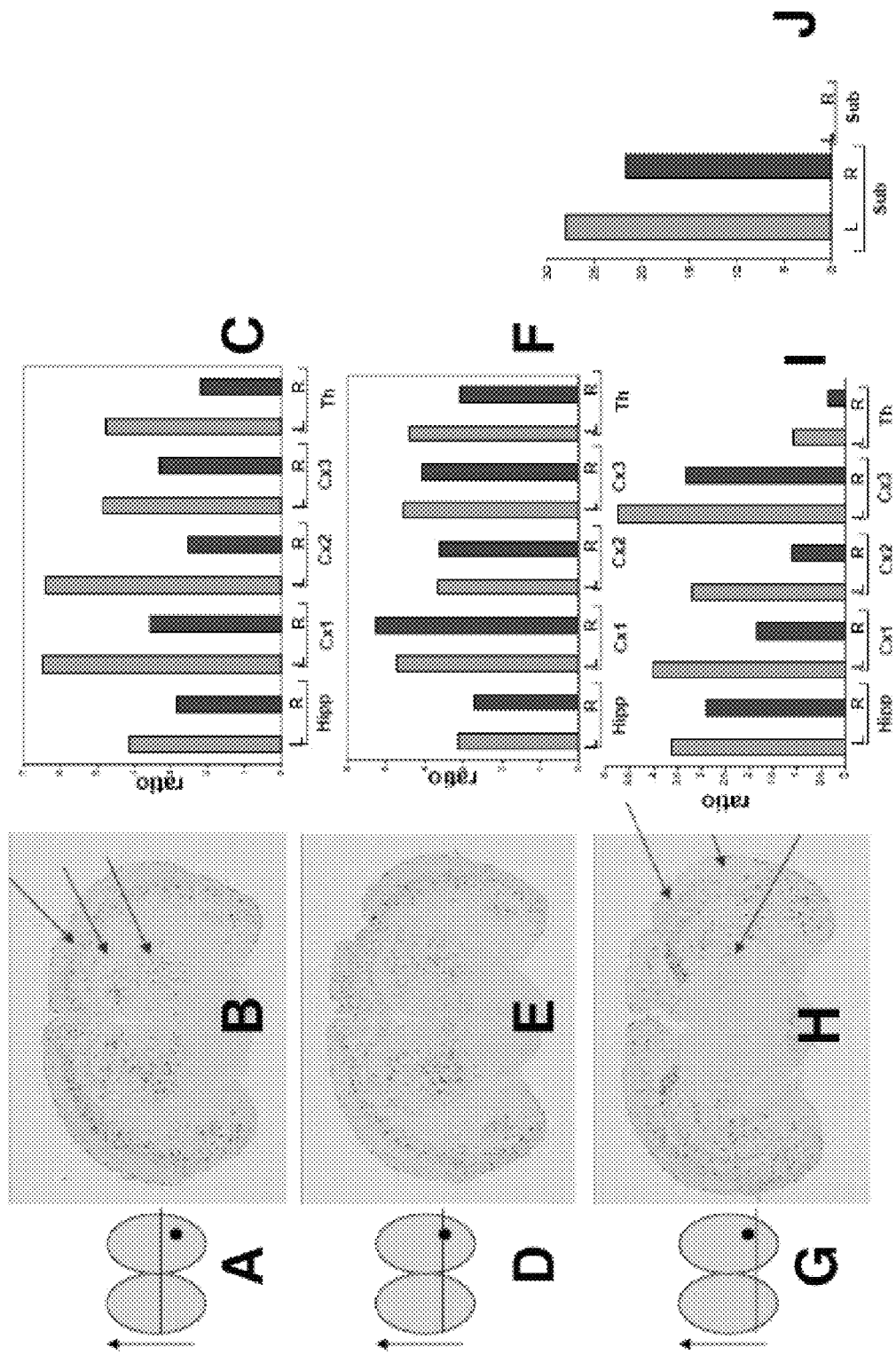
FIGS. 9A to 9J represent results from the intracranial injection (right hippocampus) of 4G8 antibody (commercial monoclonal antibody) to mice n° 47, 7 month old.
9A, 9D and 9G: position of brain sections with regard to the injection point.
9B, 9E and 9H: immunohistochemistry images of the corresponding brain sections showing amyloid peptide deposits detected with the "revealing" antibody, 6E10.
9C, 9F and 9I: amyloid peptide load calculated from images 9B, 9E and 9H, respectively, in different brain subregions in each hemisphere (Hipp: Hippocampus, Cx1: cortical region 1(dorsal), Cx2: cortical region 2 (lateral), Cx3: cortical region 3(latero-ventral), Th: thalamic). Ratio: stained area/total area of that region.
L: left, R: right (injected).
9J: amyloid peptide load calculated in subiculum in each hemisphere by immmuchemistry in the brain section H only.
Figure 10:
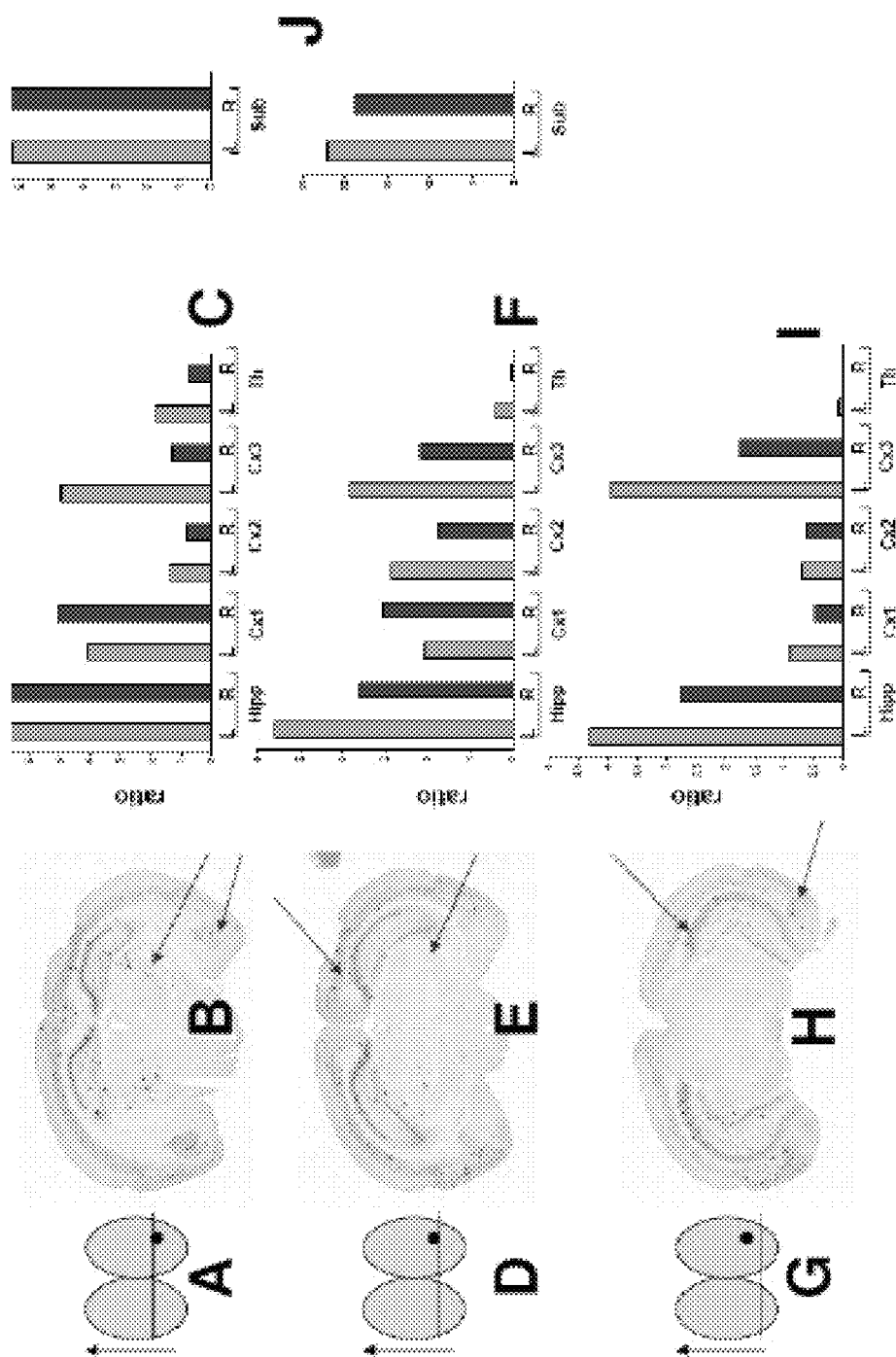
FIGS. 10A to 10J represent the intracranial injection (right hippocampus) of TeiA1.6 antibody to mice n° 17, 7 month old.
10A, 10D and 10G: position of brain section with regard to the injection point.
10B, 10E and 10H: immunohistochemistry images of the corresponding brain sections showing amyloid peptide deposits detected with the "revealing" antibody, 4G8.
10C, 10F and 10I: amyloid peptide load calculated from images 10B, 10E and 10H, respectively, in different brain subregions in each hemisphere (Hipp: Hippocampus, Cx1: cortical region 1(dorsal), Cx2: cortical region 2 (lateral), Cx3: cortical region 3(latero-ventral), Th: thalamic). Ratio: stained area/total area of that region.
L: left, R: right
10J: amyloid peptide load calculated in subiculum in each hemisphere by immmuchemistry in the brain section B and E only.
Figure 11:
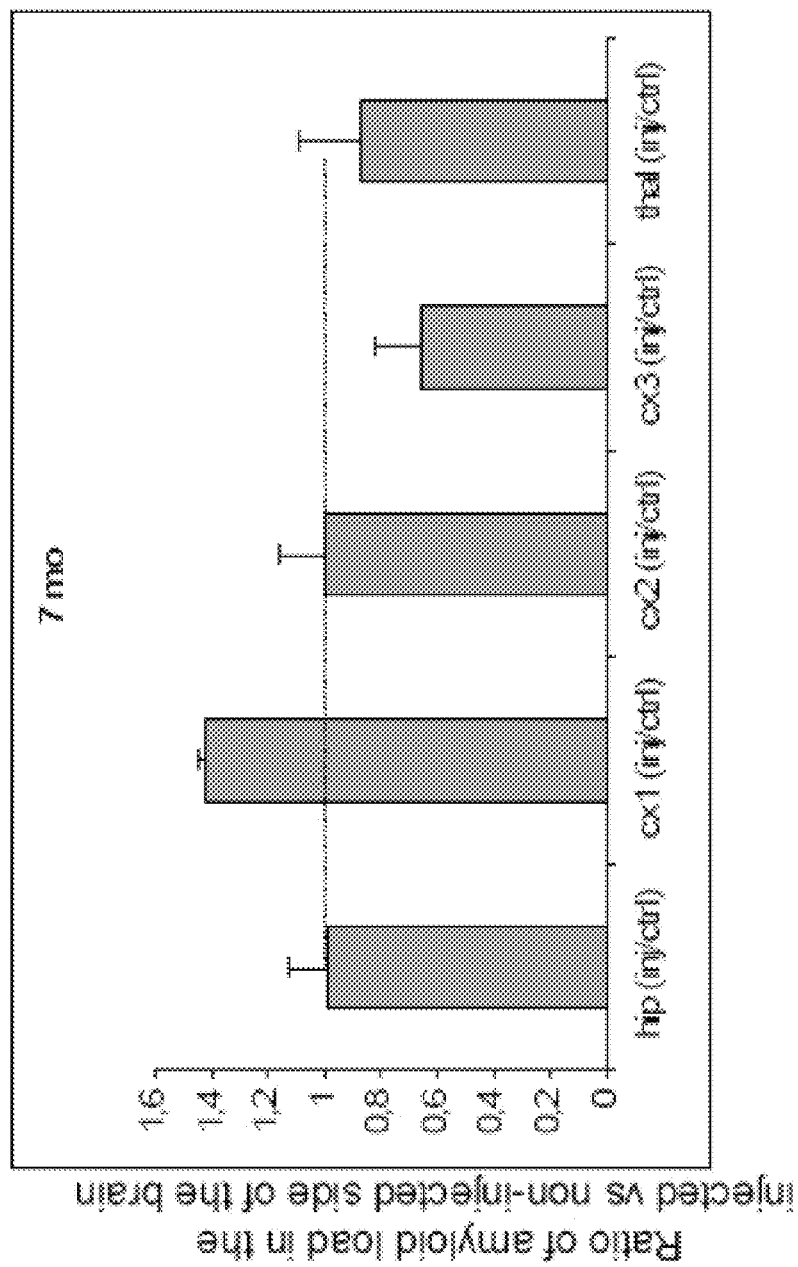
FIG. 11 represents the ratio of amyloid load between the injected (TeiA1.6 antibody) and non injected (control) in the different brain subregions (Hipp: Hippocampus, Cx1: cortical region 1(dorsal), Cx2: cortical region 2 (lateral), Cx3: cortical region 3(latero-ventral), Th: thalamic) after intracranial injection (right hippocampus) of TeiA1.6 monoclonal antibody. This is the average of ratios for 4 animals with three brain sections quantified for each (data represents means+/−SEM).

In each brain section, the amyloid peptide load was calculated in each hemisphere (injected and non-injected) in five different brain subregions [hippocampus, cortical region 1 (dorsal), cortical region 2 (lateral), cortical region 3 (lateroventral) and thalamic]. After acquisition of images on an Olympus scanner system, quantification was performed semi-automatically with the Mercator Explorallova system. For each animal, three brain sections were quantified, positioned quite similarly with regard to the injection point: one next to the injection point, one rostral and one caudal to the injection point. As previously described (Wilcock et al, 2003, J Neurosci 23:3745; Oddo et al, 2004, Neuron 43:321), 4G8 injection lead to a significant decrease in the amyloid peptide deposits in the injected hemisphere when compared to the non-injected hemisphere (FIG. 9). This effect was variable between brain sections as might be expected from this local injection of the antibody. TeiA1.6 antibody also led to a significant decrease in brain amyloid in the injected side that was more pronounced in this series of experiments in the cortical region 3 (FIG. 10). Analysis of 4 mice (aged 7 months) indicated a significant decrease (FIG. 11).

Figure 12:
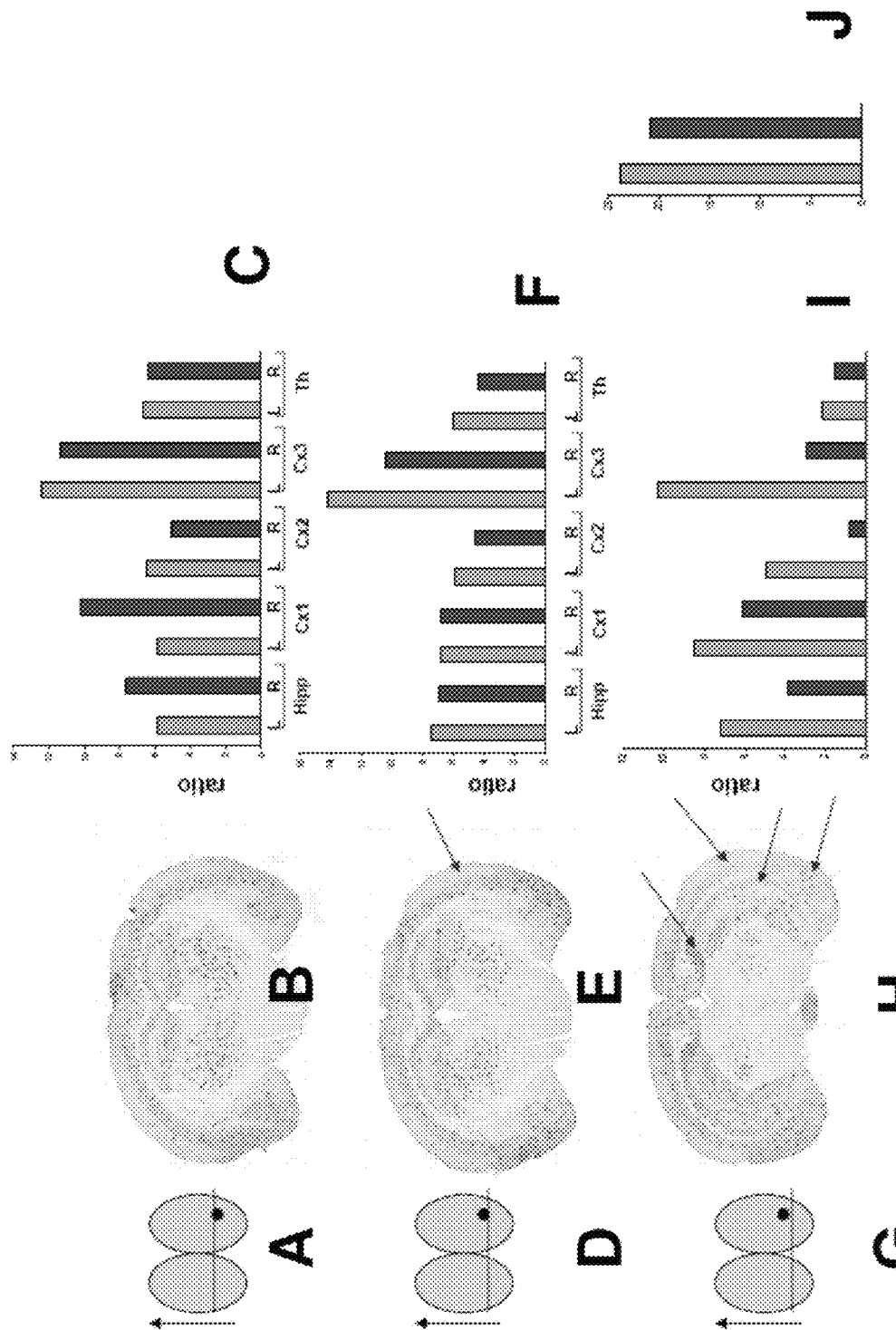
FIGS. 12A to 12J represent the intracranial injection (right hippocampus) of TeiA1.8 antibody to mice n° 58, 7 month old.
12A, 12D and 12G: position of brain section with regard to the injection point.
12B, 12E and 12H: immunohistochemistry images of the corresponding brain sections showing amyloid peptide deposits detected with the "revealing" antibody, 4G8.
12C, 12F and 12I: amyloid peptide load calculated from images 12B, 12E and 12H, respectively, in different brain subregions in each hemisphere (Hipp: Hippocampus, Cx1: cortical region 1(dorsal), Cx2: cortical region 2 (lateral), Cx3: cortical region 3(latero-ventral), Th: thalamic). Ratio: stained area/total area of that region.
L: left, R: right
12J: amyloid peptide load calculated in subiculum in each hemisphere by immmuchemistry in the brain section H only.
Figure 13:
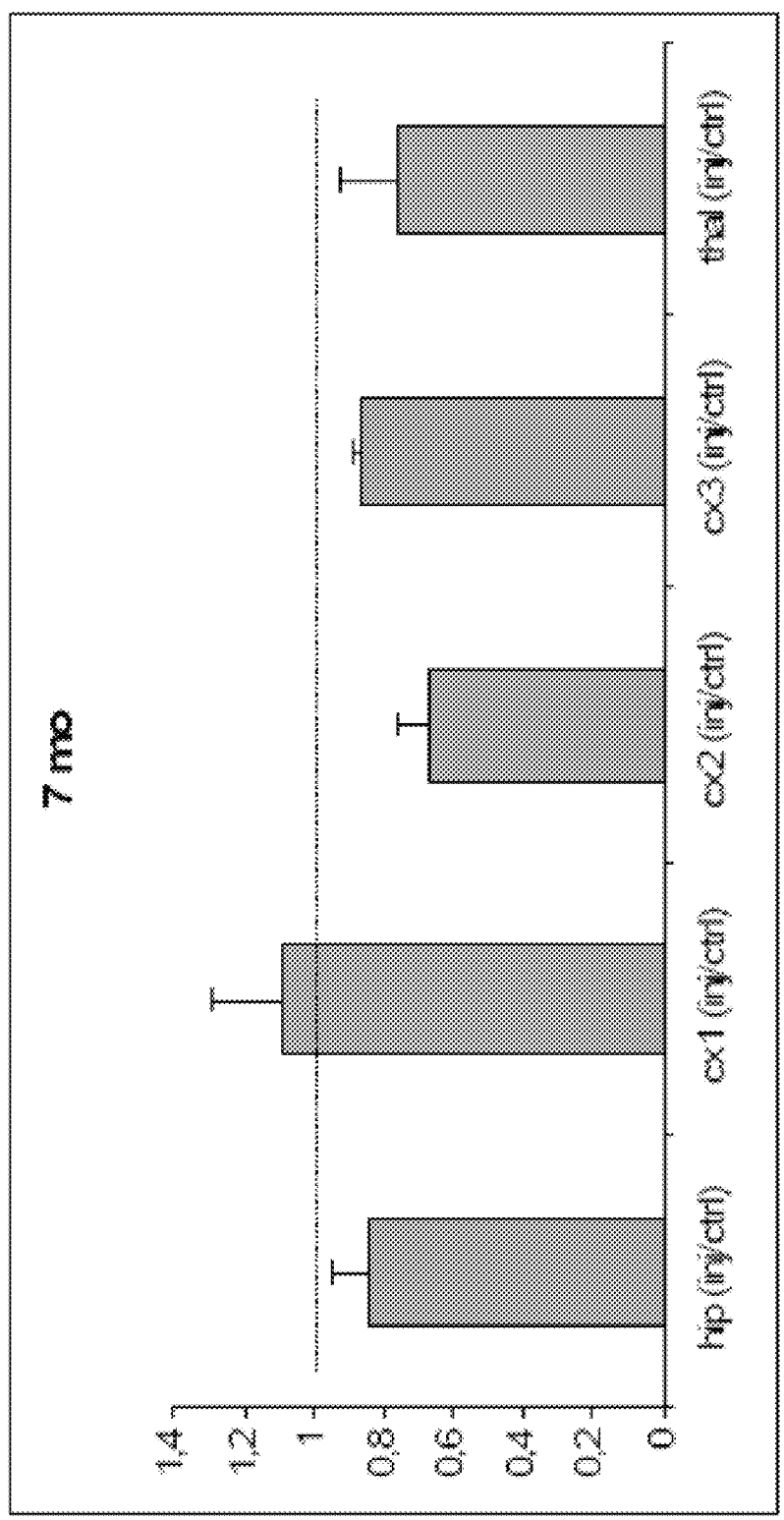
FIG. 13 represents the ratio of amyloid load between the injected (TeiA1.8 antibody) and non injected (control) in the different brain subregions (Hipp: Hippocampus, Cx1: cortical region 1(dorsal), Cx2: cortical region 2 (lateral), Cx3: cortical region 3(latero-ventral), Th: thalamic) after intracranial injection (right hippocampus) of TeiA1.6 monoclonal antibody. This is the average of ratios for 4 animals with three brain sections quantified for each (data represents means+/−SEM).

Similarly TeiA1.8 led to a significant decrease in brain amyloid in the injected side that was more pronounced in this series of experiments in the cortical region 2 (FIG. 12). Analysis of 4 mice (age 7 months) indicated a significant decrease (FIG. 13).

These data indicate that TeiA antibodies 1.6 and 1.8 decreased brain amyloid load even after short term administration and compare well with classical anti-Aβ antibodies. It is of interest to note that animals already presented a significant deposition of amyloid at the time of administration, therefore suggesting a therapeutic rather than solely preventive potential for TeiA antibodies.

TeiA antibodies could therefore provide a good therapeutic effect against amyloid load in Alzheimer Disease patients.

---

The invention claimed is:

1. A monoclonal antibody, Antibody TeiA 1.6, comprising:
   a light chain variable region: SSLTVTAGEKVTM-SCKSSQSLLAGRYQKNYLTWYQQKPGQP-PKLLIYWASTRDSGVPDRFTGSGS GTDFTLTISS-VQAEDLAVYYCQNDYTYPLTFAG (SEQ ID NO:1), wherein complementarity determining regions of the light chain variable region (CDR-L) comprise the following sequences:
   CDR-L1: KSSQSLLAGRYQKNYLT (SEQ ID NO : 11)
   CDR-L2: WASTRDSG (SEQ ID NO : 12)
   CDR-L3: QNDYTYPLT (SEQ ID NO : 13); and
   a heavy chain variable region: GGLVQPGGSLRLSCAIS-GFTFSDFYMEWVRQPPGKRLEWIAASRN-KANDYTTEYSASVKGRFIVS RDTSQSILYLQM-NALRAEDTAIYYCATYHDYAMDYWGQGTSVTVSS (SEQ ID NO:2), wherein complementarity determining regions of the heavy chain variable region (CDR-H) comprise the following sequences:
   CDR-H1: GFTFSDFYME (SEQ ID NO : 14)
   CDR-H2: ASRNKANDYTTEYSASVKG (SEQ ID NO : 15), and
   CDR-H3: YHDYAMDY (SEQ ID NO : 16),
   wherein said monoclonal antibody specifically binds to the N-terminal region of $A\beta_{8-x}$ peptide, x being comprised from 15 to 42, and recognises neither $A\beta_{1-40}$ nor $A\beta_{1-42}$.

2. The monoclonal antibody according to claim 1, wherein said antibody presents a high specificity for the free N-terminal end of $A\beta_{8-x}$ peptide.

3. The monoclonal antibody according to claim 1, wherein said antibody presents a high affinity with respect to $A\beta_{8-x}$ peptide.

4. The monoclonal antibody according to claim 1, wherein said antibody specifically targets parenchymal amyloid deposits of $A\beta_{8-x}$ peptide in the brain and does not interact with vascular amyloid deposits.

5. The monoclonal antibody according to claim 1, wherein said antibody is labelled with a compound chosen from the group comprising: a radionuclide, a fluorophore, an enzyme label, an enzyme substrate, an enzyme co-factor, enzyme inhibitor and a hapten.

6. The monoclonal antibody according to claim 1, which is a humanised antibody.

7. A hybridoma producing a monoclonal antibody according to claim 1.

8. The hybridoma according to claim 7, wherein said hybridoma have been deposited on Aug. 23, 2007,
   at:
   BCCM/LMBP Plasmid Collection under the following Accession No:
   TeiA 1.6 or 2.6F4C2(IGH521)-->LMBP 6594CB.

9. A kit comprising at least one buffer, and at least one detection compound, said at least one detection compound being at least one N-truncated $A\beta_{8-x}$ specific antibody as defined in claim 1.

10. The kit of claim 9, further comprising a labelled second antibody which binds to an antibody which specifically binds to the N-terminal region of $A\beta_{8-x}$ peptide, x being comprised from 15 to 42, and recognises neither $A\beta_{1-40}$ nor $A\beta_{1-42}$.

11. A therapeutic composition comprising as an active ingredient a monoclonal antibody of claim 1 in association with a pharmaceutically acceptable vehicle.

12. The therapeutic composition of claim 11 being suitable for the administration to an individual of a dose of a monoclonal antibody from 1 mg/kg/day to 200 mg /kg/day.

13. A vaccine composition comprising as an active ingredient a monoclonal antibody of claim 1, or epitope binding fragments thereof, in association with a pharmaceutically acceptable vehicle.

14. The vaccine composition of claim 13 being suitable for the administration to an individual of a dose of a monoclonal antibody from 1 mg/kg/day to 200 mg /kg/day.

15. A method for the treatment of Alzheimer's disease in a patient, comprising administering monoclonal antibodies of claim 1 to the patient.

16. A method for the clearance of β-amyloid burden in the brain of a patient comprising administering monoclonal antibodies of claim 1 to the patient.

17. A method for the clearance of b-amyloid burden in the brain of a mammal comprising administering a composition of claim 11 to the mammal.

* * * * *

SEQUENCE LISTING

```
<160> NUMBER OF SEQ ID NOS: 37

<210> SEQ ID NO 1
<211> LENGTH: 98
<212> TYPE: PRT
<213> ORGANISM: mouse
<220> FEATURE:
<221> NAME/KEY: PEPTIDE
<222> LOCATION: (1)..(98)

<400> SEQUENCE: 1

Ser Ser Leu Thr Val Thr Ala Gly Glu Lys Val Thr Met Ser Cys Lys
1               5                   10                  15

Ser Ser Gln Ser Leu Leu Ala Gly Arg Tyr Gln Lys Asn Tyr Leu Thr
            20                  25                  30

Trp Tyr Gln Gln Lys Pro Gly Gln Pro Pro Lys Leu Leu Ile Tyr Trp
        35                  40                  45

Ala Ser Thr Arg Asp Ser Gly Val Pro Asp Arg Phe Thr Gly Ser Gly
    50                  55                  60

Ser Gly Thr Asp Phe Thr Leu Thr Ile Ser Ser Val Gln Ala Glu Asp
65                  70                  75                  80

Leu Ala Val Tyr Tyr Cys Gln Asn Asp Tyr Thr Tyr Pro Leu Thr Phe
                85                  90                  95

Ala Gly

<210> SEQ ID NO 2
<211> LENGTH: 111
<212> TYPE: PRT
<213> ORGANISM: mouse
<220> FEATURE:
<221> NAME/KEY: PEPTIDE
<222> LOCATION: (1)..(111)

<400> SEQUENCE: 2

Gly Gly Leu Val Gln Pro Gly Gly Ser Leu Arg Leu Ser Cys Ala Ile
1               5                   10                  15

Ser Gly Phe Thr Phe Ser Asp Phe Tyr Met Glu Trp Val Arg Gln Pro
            20                  25                  30
```

```
Pro Gly Lys Arg Leu Glu Trp Ile Ala Ala Ser Arg Asn Lys Ala Asn
            35                  40                  45

Asp Tyr Thr Thr Glu Tyr Ser Ala Ser Val Lys Gly Arg Phe Ile Val
    50                  55                  60

Ser Arg Asp Thr Ser Gln Ser Ile Leu Tyr Leu Gln Met Asn Ala Leu
65                  70                  75                  80

Arg Ala Glu Asp Thr Ala Ile Tyr Tyr Cys Ala Thr Tyr His Asp Tyr
                85                  90                  95

Ala Met Asp Tyr Trp Gly Gln Gly Thr Ser Val Thr Val Ser Ser
                100                 105                 110
```

```
<210> SEQ ID NO 3
<211> LENGTH: 99
<212> TYPE: PRT
<213> ORGANISM: Mouse
<220> FEATURE:
<221> NAME/KEY: PEPTIDE
<222> LOCATION: (1)..(99)

<400> SEQUENCE: 3

Ser Ser Leu Thr Val Thr Ala Gly Glu Lys Val Thr Met Asn Cys Lys
1               5                   10                  15

Ser Ser Gln Asn Leu Leu Asn Ser Gly Asn Gln Val Asn Tyr Leu Thr
            20                  25                  30

Trp Phe Gln Gln Lys Pro Gly Gln Pro Pro Lys Leu Leu Ile Tyr Trp
            35                  40                  45

Ala Ser Thr Arg Glu Ser Gly Val Pro Asp Arg Phe Ile Gly Ser Gly
    50                  55                  60

Ser Gly Thr Asp Phe Thr Leu Thr Ile Asn Ser Val Gln Ala Glu Asp
65                  70                  75                  80

Leu Ala Val Tyr Tyr Cys Gln Asn Asp Tyr Arg Tyr Pro Leu Thr Phe
                85                  90                  95

Gly Ala Gly
```

```
<210> SEQ ID NO 4
<211> LENGTH: 111
<212> TYPE: PRT
<213> ORGANISM: Mouse
<220> FEATURE:
<221> NAME/KEY: PEPTIDE
<222> LOCATION: (1)..(111)

<400> SEQUENCE: 4

Gly Gly Leu Val Gln Pro Gly Gly Ser Leu Arg Leu Ser Cys Ala Thr
1               5                   10                  15

Ser Gly Phe Thr Phe Ser Asp Phe Tyr Met Glu Trp Val Arg Gln Pro
            20                  25                  30

Pro Gly Arg Arg Leu Glu Trp Ile Ala Ala Ser Arg Asp Lys Ala Lys
            35                  40                  45

Asp Tyr Thr Thr Glu Tyr Ser Ala Ser Val Lys Gly Arg Phe Ile Val
    50                  55                  60

Ser Arg Asp Thr Ser Gln Ser Ile Phe Tyr Leu Gln Met Asn Ala Leu
65                  70                  75                  80

Arg Ser Glu Asp Thr Ala Ile Tyr Tyr Cys Ala Thr Tyr Phe Ser Tyr
                85                  90                  95

Ala Met Asp Tyr Trp Gly Leu Gly Thr Ser Val Thr Val Ser Ser
                100                 105                 110
```

```
<210> SEQ ID NO 5
```

```
<211> LENGTH: 99
<212> TYPE: PRT
<213> ORGANISM: Mouse
<220> FEATURE:
<221> NAME/KEY: PEPTIDE
<222> LOCATION: (1)..(99)

<400> SEQUENCE: 5

Ser Ser Leu Ala Val Thr Ala Gly Glu Arg Val Thr Met Ser Cys Lys
1               5                   10                  15

Ser Ser Leu Thr Leu Leu Asn Ser Gly Ser Gln Thr Asn Tyr Leu Thr
            20                  25                  30

Trp Tyr Gln Gln Lys Pro Gly Gln Pro Pro Lys Leu Leu Ile Tyr Trp
        35                  40                  45

Ala Ser Thr Arg Glu Ser Gly Val Pro Asp Arg Phe Thr Gly Ser Gly
    50                  55                  60

Ser Gly Thr Asp Phe Thr Leu Thr Ile Ser Ser Val Gln Ala Glu Asp
65                  70                  75                  80

Leu Ala Val Tyr Tyr Cys Gln Asn Asp Tyr Ser Tyr Pro Leu Thr Phe
                85                  90                  95

Gly Ala Gly

<210> SEQ ID NO 6
<211> LENGTH: 110
<212> TYPE: PRT
<213> ORGANISM: Mouse
<220> FEATURE:
<221> NAME/KEY: PEPTIDE
<222> LOCATION: (1)..(110)

<400> SEQUENCE: 6

Gly Gly Leu Val Gln Pro Gly Gly Ser Leu Arg Leu Ser Cys Ala Thr
1               5                   10                  15

Ala Gly Phe Thr Phe Thr Asp Gln Tyr Met Ser Trp Val Arg Gln Pro
            20                  25                  30

Pro Gly Lys Ala Leu Glu Trp Leu Ala Thr Ile Arg Asn Lys Ala Lys
        35                  40                  45

Gly Phe Thr Thr Glu Tyr Ser Ala Ser Val Lys Gly Arg Phe Thr Ile
    50                  55                  60

Ser Arg Asp Asn Ser Gln Ser Ile Leu Tyr Leu Gln Met Ser Thr Leu
65                  70                  75                  80

Arg Ala Gly Asp Ser Ala Thr Tyr Tyr Cys Ala Val Tyr Gly Asn Tyr
                85                  90                  95

Ala Met Asp Tyr Trp Gly Gln Gly Thr Ser Val Asn Val Ser
            100                 105                 110

<210> SEQ ID NO 7
<211> LENGTH: 99
<212> TYPE: PRT
<213> ORGANISM: Mouse
<220> FEATURE:
<221> NAME/KEY: PEPTIDE
<222> LOCATION: (1)..(99)

<400> SEQUENCE: 7

Ser Ser Leu Thr Val Thr Ala Gly Glu Lys Val Thr Met Ser Cys Lys
1               5                   10                  15

Ser Ser Gln Ser Leu Phe Asn Ser Gly Arg Gln Thr Asn Tyr Leu Thr
            20                  25                  30

Trp Phe Gln Gln Arg Pro Gly Gln Ala Pro Lys Leu Leu Ile Tyr Trp
        35                  40                  45
```

```
Ala Ser Thr Arg Gly Ser Gly Val Pro Asp Arg Phe Thr Gly Ser Gly
        50                  55                  60

Ser Gly Thr Glu Phe Thr Leu Thr Ile Ser Ser Val Gln Ala Glu Asp
 65                  70                  75                  80

Leu Ala Val Tyr Tyr Cys Gln Asn Asp Tyr Thr Tyr Pro Leu Thr Phe
                 85                  90                  95

Gly Ala Gly

<210> SEQ ID NO 8
<211> LENGTH: 111
<212> TYPE: PRT
<213> ORGANISM: Mouse
<220> FEATURE:
<221> NAME/KEY: PEPTIDE
<222> LOCATION: (1)..(110)
<220> FEATURE:
<221> NAME/KEY: PEPTIDE
<222> LOCATION: (1)..(111)

<400> SEQUENCE: 8

Gly Gly Leu Val Gln Pro Gly Gly Ser Leu Arg Leu Ser Cys Ala Thr
 1               5                  10                  15

Ser Gly Phe Thr Phe Thr Asp Phe Tyr Met Glu Trp Val Arg Gln Pro
                20                  25                  30

Pro Gly Lys Arg Leu Glu Trp Ile Ala Ala Ser Arg Asn Lys Ala Asn
                35                  40                  45

Gly Tyr Thr Thr Glu Tyr Ser Ala Ser Val Lys Gly Arg Phe Ile Val
         50                  55                  60

Ser Arg Asp Thr Ser Gln Gly Ile Leu Tyr Leu Gln Met Ser Ala Leu
 65                  70                  75                  80

Arg Ala Glu Asp Thr Ala Ile Tyr Tyr Cys Ala Ile Tyr Arg Tyr Tyr
                 85                  90                  95

Ala Met Asp Tyr Trp Gly Gln Gly Thr Ser Val Thr Val Ser Ser
                100                 105                 110

<210> SEQ ID NO 9
<211> LENGTH: 99
<212> TYPE: PRT
<213> ORGANISM: Mouse
<220> FEATURE:
<221> NAME/KEY: PEPTIDE
<222> LOCATION: (1)..(99)

<400> SEQUENCE: 9

Ser Ser Leu Thr Val Thr Ala Gly Glu Lys Val Thr Met Ser Cys Thr
 1               5                  10                  15

Ser Ser Gln Ser Leu Phe Asn Ser Gly Thr Gln Thr Asn Tyr Leu Thr
                20                  25                  30

Trp Tyr Gln Gln Lys Pro Gly Gln Pro Pro Lys Leu Leu Ile Tyr Trp
                35                  40                  45

Ala Ser Thr Arg Glu Ser Gly Val Pro Asp Arg Phe Thr Gly Ser Gly
         50                  55                  60

Ser Gly Thr Asp Phe Thr Leu Thr Ile Ser Ser Val Gln Ala Glu Asp
 65                  70                  75                  80

Leu Ala Val Tyr Tyr Cys Gln Asn Asp Tyr Thr Tyr Pro Leu Thr Phe
                 85                  90                  95

Gly Ala Gly

<210> SEQ ID NO 10
```

```
<211> LENGTH: 111
<212> TYPE: PRT
<213> ORGANISM: Mouse
<220> FEATURE:
<221> NAME/KEY: PEPTIDE
<222> LOCATION: (1)..(111)

<400> SEQUENCE: 10

Gly Gly Leu Val Gln Pro Gly Gly Ser Leu Arg Leu Ser Cys Ala Thr
1               5                   10                  15

Ser Gly Phe Thr Phe Ser Asp Phe Phe Ile Glu Trp Val Arg Gln Pro
            20                  25                  30

Pro Gly Lys Arg Leu Glu Trp Ile Thr Ala Ser Arg Asn Lys Asn Tyr
        35                  40                  45

Asp Tyr Lys Thr Glu Tyr Ser Ala Ser Val Lys Gly Arg Phe Ile Val
    50                  55                  60

Ser Arg Asp Thr Ser Gln Ser Ile Leu Tyr Leu Gln Met Asn Ala Leu
65                  70                  75                  80

Arg Ala Glu Asp Thr Ala Ile Tyr Tyr Cys Ala Ile Tyr Arg His Tyr
                85                  90                  95

Ala Met Asp Tyr Trp Gly Gln Gly Thr Ser Val Thr Val Ser Ser
            100                 105                 110

<210> SEQ ID NO 11
<211> LENGTH: 17
<212> TYPE: PRT
<213> ORGANISM: Mouse
<220> FEATURE:
<221> NAME/KEY: PEPTIDE
<222> LOCATION: (1)..(17)

<400> SEQUENCE: 11

Lys Ser Ser Gln Ser Leu Leu Ala Gly Arg Tyr Gln Lys Asn Tyr Leu
1               5                   10                  15

Thr

<210> SEQ ID NO 12
<211> LENGTH: 8
<212> TYPE: PRT
<213> ORGANISM: Mouse
<220> FEATURE:
<221> NAME/KEY: PEPTIDE
<222> LOCATION: (1)..(8)

<400> SEQUENCE: 12

Trp Ala Ser Thr Arg Asp Ser Gly
1               5

<210> SEQ ID NO 13
<211> LENGTH: 9
<212> TYPE: PRT
<213> ORGANISM: Mouse
<220> FEATURE:
<221> NAME/KEY: PEPTIDE
<222> LOCATION: (1)..(9)

<400> SEQUENCE: 13

Gln Asn Asp Tyr Thr Tyr Pro Leu Thr
1               5

<210> SEQ ID NO 14
<211> LENGTH: 10
<212> TYPE: PRT
<213> ORGANISM: Mouse
<220> FEATURE:
```

```
<221> NAME/KEY: PEPTIDE
<222> LOCATION: (1)..(10)

<400> SEQUENCE: 14

Gly Phe Thr Phe Ser Asp Phe Tyr Met Glu
1               5                   10

<210> SEQ ID NO 15
<211> LENGTH: 19
<212> TYPE: PRT
<213> ORGANISM: Mouse
<220> FEATURE:
<221> NAME/KEY: PEPTIDE
<222> LOCATION: (1)..(19)

<400> SEQUENCE: 15

Ala Ser Arg Asn Lys Ala Asn Asp Tyr Thr Thr Glu Tyr Ser Ala Ser
1               5                   10                  15

Val Lys Gly

<210> SEQ ID NO 16
<211> LENGTH: 8
<212> TYPE: PRT
<213> ORGANISM: Mouse
<220> FEATURE:
<221> NAME/KEY: PEPTIDE
<222> LOCATION: (1)..(8)

<400> SEQUENCE: 16

Tyr His Asp Tyr Ala Met Asp Tyr
1               5

<210> SEQ ID NO 17
<211> LENGTH: 17
<212> TYPE: PRT
<213> ORGANISM: Mouse
<220> FEATURE:
<221> NAME/KEY: PEPTIDE
<222> LOCATION: (1)..(17)

<400> SEQUENCE: 17

Lys Ser Ser Gln Asn Leu Leu Asn Ser Gly Asn Gln Val Asn Tyr Leu
1               5                   10                  15

Thr

<210> SEQ ID NO 18
<211> LENGTH: 8
<212> TYPE: PRT
<213> ORGANISM: Mouse
<220> FEATURE:
<221> NAME/KEY: PEPTIDE
<222> LOCATION: (1)..(8)

<400> SEQUENCE: 18

Trp Ala Ser Thr Arg Glu Ser Gly
1               5

<210> SEQ ID NO 19
<211> LENGTH: 9
<212> TYPE: PRT
<213> ORGANISM: Mouse
<220> FEATURE:
<221> NAME/KEY: PEPTIDE
<222> LOCATION: (1)..(9)

<400> SEQUENCE: 19

Gln Asn Asp Tyr Arg Tyr Pro Leu Thr
```

<210> SEQ ID NO 20
<211> LENGTH: 8
<212> TYPE: PRT
<213> ORGANISM: Mouse
<220> FEATURE:
<221> NAME/KEY: PEPTIDE
<222> LOCATION: (1)..(8)

<400> SEQUENCE: 20

Tyr Phe Ser Tyr Ala Met Asp Tyr
1               5

<210> SEQ ID NO 21
<211> LENGTH: 17
<212> TYPE: PRT
<213> ORGANISM: Mouse
<220> FEATURE:
<221> NAME/KEY: PEPTIDE
<222> LOCATION: (1)..(17)

<400> SEQUENCE: 21

Lys Ser Ser Leu Thr Leu Leu Asn Ser Gly Ser Gln Thr Asn Tyr Leu
1               5                   10                  15

Thr

<210> SEQ ID NO 22
<211> LENGTH: 9
<212> TYPE: PRT
<213> ORGANISM: Mouse
<220> FEATURE:
<221> NAME/KEY: PEPTIDE
<222> LOCATION: (1)..(9)

<400> SEQUENCE: 22

Gln Asn Asp Tyr Ser Tyr Pro Leu Thr
1               5

<210> SEQ ID NO 23
<211> LENGTH: 10
<212> TYPE: PRT
<213> ORGANISM: Mouse
<220> FEATURE:
<221> NAME/KEY: PEPTIDE
<222> LOCATION: (1)..(10)

<400> SEQUENCE: 23

Gly Phe Thr Phe Thr Asp Gln Tyr Met Ser
1               5                   10

<210> SEQ ID NO 24
<211> LENGTH: 19
<212> TYPE: PRT
<213> ORGANISM: Mouse
<220> FEATURE:
<221> NAME/KEY: PEPTIDE
<222> LOCATION: (1)..(19)

<400> SEQUENCE: 24

Thr Ile Arg Asn Lys Ala Lys Gly Phe Thr Thr Glu Tyr Ser Ala Ser
1               5                   10                  15

Val Lys Gly

<210> SEQ ID NO 25
<211> LENGTH: 8
<212> TYPE: PRT

```
<213> ORGANISM: Mouse
<220> FEATURE:
<221> NAME/KEY: PEPTIDE
<222> LOCATION: (1)..(8)

<400> SEQUENCE: 25

Tyr Gly Asn Tyr Ala Met Asp Tyr
1               5

<210> SEQ ID NO 26
<211> LENGTH: 17
<212> TYPE: PRT
<213> ORGANISM: Mouse
<220> FEATURE:
<221> NAME/KEY: PEPTIDE
<222> LOCATION: (1)..(17)

<400> SEQUENCE: 26

Lys Ser Ser Gln Ser Leu Phe Asn Ser Gly Arg Gln Thr Asn Tyr Leu
1               5                   10                  15

Thr

<210> SEQ ID NO 27
<211> LENGTH: 7
<212> TYPE: PRT
<213> ORGANISM: Mouse
<220> FEATURE:
<221> NAME/KEY: PEPTIDE
<222> LOCATION: (1)..(7)

<400> SEQUENCE: 27

Trp Ala Ser Thr Arg Gly Ser
1               5

<210> SEQ ID NO 28
<211> LENGTH: 10
<212> TYPE: PRT
<213> ORGANISM: mouse
<220> FEATURE:
<221> NAME/KEY: PEPTIDE
<222> LOCATION: (1)..(10)

<400> SEQUENCE: 28

Gly Phe Thr Phe Thr Asp Phe Tyr Met Glu
1               5                   10

<210> SEQ ID NO 29
<211> LENGTH: 19
<212> TYPE: PRT
<213> ORGANISM: mouse
<220> FEATURE:
<221> NAME/KEY: PEPTIDE
<222> LOCATION: (1)..(19)

<400> SEQUENCE: 29

Ala Ser Arg Asn Lys Ala Asn Gly Tyr Thr Thr Glu Tyr Ser Ala Ser
1               5                   10                  15

Val Lys Gly

<210> SEQ ID NO 30
<211> LENGTH: 8
<212> TYPE: PRT
<213> ORGANISM: mouse
<220> FEATURE:
<221> NAME/KEY: PEPTIDE
<222> LOCATION: (1)..(8)

<400> SEQUENCE: 30
```

```
Tyr Arg Tyr Tyr Ala Met Asp Tyr
1               5
```

<210> SEQ ID NO 31
<211> LENGTH: 17
<212> TYPE: PRT
<213> ORGANISM: mouse
<220> FEATURE:
<221> NAME/KEY: PEPTIDE
<222> LOCATION: (1)..(17)

<400> SEQUENCE: 31

```
Thr Ser Ser Gln Ser Leu Phe Asn Ser Gly Thr Gln Thr Asn Tyr Leu
1               5                  10                  15

Thr
```

<210> SEQ ID NO 32
<211> LENGTH: 10
<212> TYPE: PRT
<213> ORGANISM: mouse
<220> FEATURE:
<221> NAME/KEY: PEPTIDE
<222> LOCATION: (1)..(10)

<400> SEQUENCE: 32

```
Gly Phe Thr Phe Ser Asp Phe Phe Ile Glu
1               5                  10
```

<210> SEQ ID NO 33
<211> LENGTH: 19
<212> TYPE: PRT
<213> ORGANISM: mouse
<220> FEATURE:
<221> NAME/KEY: PEPTIDE
<222> LOCATION: (1)..(19)

<400> SEQUENCE: 33

```
Ala Ser Arg Asn Lys Asn Tyr Asp Tyr Lys Thr Glu Tyr Ser Ala Ser
1               5                  10                  15

Val Lys Gly
```

<210> SEQ ID NO 34
<211> LENGTH: 8
<212> TYPE: PRT
<213> ORGANISM: mouse
<220> FEATURE:
<221> NAME/KEY: PEPTIDE
<222> LOCATION: (1)..(8)

<400> SEQUENCE: 34

```
Tyr Arg His Tyr Ala Met Asp Tyr
1               5
```

<210> SEQ ID NO 35
<211> LENGTH: 19
<212> TYPE: PRT
<213> ORGANISM: mouse
<220> FEATURE:
<221> NAME/KEY: PEPTIDE
<222> LOCATION: (1)..(19)

<400> SEQUENCE: 35

```
Ala Ser Arg Asp Lys Ala Lys Asp Tyr Thr Thr Glu Tyr Ser Ala Ser
1               5                  10                  15

Val Lys Gly
```

```
<210> SEQ ID NO 36
<211> LENGTH: 12
<212> TYPE: PRT
<213> ORGANISM: mouse
<220> FEATURE:
<221> NAME/KEY: PEPTIDE
<222> LOCATION: (1)..(12)

<400> SEQUENCE: 36

Ser Gly Tyr Gly Val His His Gly Cys Lys Leu His
1               5                   10

<210> SEQ ID NO 37
<211> LENGTH: 48
<212> TYPE: PRT
<213> ORGANISM: mouse
<220> FEATURE:
<221> NAME/KEY: PEPTIDE
<222> LOCATION: (1)..(48)

<400> SEQUENCE: 37

Ser Glu Val Lys Met Asp Ala Glu Phe Arg His Asp Ser Gly Tyr Glu
1               5                   10                  15

Val His His Gln Lys Leu Val Phe Phe Ala Glu Asp Val Gly Ser Asn
            20                  25                  30

Lys Gly Ala Ile Ile Gly Leu Met Val Gly Gly Val Val Ile Ala Thr
        35                  40                  45
```